(12) United States Patent
Tian et al.

(10) Patent No.: US 11,857,491 B2
(45) Date of Patent: Jan. 2, 2024

(54) INTEGRATED COLD THERAPY-COMPRESSION THERAPY ASSEMBLY AND ASSOCIATED TREATMENT PROTOCOLS

(71) Applicant: Breg, Inc., Carlsbad, CA (US)

(72) Inventors: Amanda Y Tian, San Diego, CA (US); Veronica M Mora, San Diego, CA (US); Michael G Johnson, San Marcos, CA (US)

(73) Assignee: Breg, Inc., Carlsbad, CA (US)

( * ) Notice: Subject to any disclaimer, the term of this patent is extended or adjusted under 35 U.S.C. 154(b) by 966 days.

(21) Appl. No.: 16/817,141

(22) Filed: Mar. 12, 2020

(65) Prior Publication Data
US 2020/0289361 A1    Sep. 17, 2020

Related U.S. Application Data

(60) Provisional application No. 62/818,091, filed on Mar. 13, 2019.

(51) Int. Cl.
*A61H 9/00* (2006.01)
*A61F 7/00* (2006.01)

(52) U.S. Cl.
CPC ......... *A61H 9/0092* (2013.01); *A61F 7/0085* (2013.01); *A61F 2007/0042* (2013.01); *A61F 2007/0056* (2013.01); *A61H 2201/0207* (2013.01); *A61H 2201/0214* (2013.01); *A61H 2201/0242* (2013.01); *A61H 2201/5023* (2013.01); *A61H 2201/5071* (2013.01); *A61H 2205/102* (2013.01)

(58) Field of Classification Search
CPC .... A61B 2090/064; A61F 7/0085; A61F 7/02; A61F 2007/0042; A61F 2007/0056; A61F 2007/0093; A61F 2007/0231; A61H 1/00; A61H 9/0092; A61H 2201/0207; A61H 2201/0214; A61H 2201/0242; A61H 2201/5023; A61H 2201/5071; A61H 2205/102
See application file for complete search history.

(56) References Cited

U.S. PATENT DOCUMENTS

| | | | |
|---|---|---|---|
| 2,533,504 A | 12/1950 | Poor | |
| 3,456,270 A | 7/1969 | Weinstein | |
| 3,548,819 A | 12/1970 | Davis | |
| 3,803,647 A | 4/1974 | Reswick | |
| 3,967,627 A * | 7/1976 | Brown | A61F 7/02 607/104 |
| 4,168,555 A | 9/1979 | Benjamin | |
| 4,310,936 A | 1/1982 | Benjamin | |
| 4,457,295 A | 7/1984 | Roehr | |
| 4,558,476 A | 12/1985 | Linder | |
| 4,738,119 A | 4/1988 | Zafred | |

(Continued)

*Primary Examiner* — Colin W Stuart
*Assistant Examiner* — Matthew D Ziegler
(74) *Attorney, Agent, or Firm* — Rodney F. Brown

(57) ABSTRACT

A single integrated cold therapy-compression therapy assembly combines a cold therapy module designed to apply cold therapy in a continuous mode and a compression therapy module designed to apply compression therapy in an intermittent mode to select body parts of a user in accordance with associated integrated therapeutic treatment protocols. The body part selected for therapy is dependent on the particular needs of the user.

20 Claims, 14 Drawing Sheets

(56) References Cited

U.S. PATENT DOCUMENTS

| | | | |
|---|---|---|---|
| 4,901,386 A | 2/1990 | Lane | |
| 5,044,030 A | 9/1991 | Balaton | |
| 5,172,689 A | 12/1992 | Wright | |
| 5,230,335 A | 7/1993 | Johnson, Jr. | |
| 5,241,971 A | 9/1993 | Mason | |
| 5,314,455 A | 5/1994 | Johnson, Jr. | |
| 5,402,542 A * | 4/1995 | Viard | A61G 7/05746 |
| | | | 5/421 |
| 5,411,541 A | 5/1995 | Bell | |
| 5,466,250 A | 11/1995 | Johnson, Jr. | |
| 5,584,798 A | 12/1996 | Fox | |
| 5,588,955 A | 12/1996 | Johnson, Jr. | |
| 5,634,940 A | 6/1997 | Panyard | |
| 5,669,872 A | 9/1997 | Fox | |
| 5,755,755 A | 5/1998 | Panyard | |
| 5,792,216 A | 8/1998 | Kappel | |
| 5,850,644 A | 12/1998 | Hsia | |
| 5,862,675 A * | 1/1999 | Scaringe | A62B 17/005 |
| | | | 62/196.3 |
| 5,980,561 A | 11/1999 | Kolen | |
| 5,989,285 A | 11/1999 | DeVilbiss | |
| 6,007,559 A | 12/1999 | Arkans | |
| 6,178,562 B1 | 1/2001 | Elkins | |
| 6,295,819 B1 * | 10/2001 | Mathiprakasam | F25B 21/02 |
| | | | 62/3.5 |
| 6,447,467 B1 | 9/2002 | Barak | |
| 6,478,757 B1 | 11/2002 | Barak | |
| 6,551,347 B1 * | 4/2003 | Elkins | A61F 7/02 |
| | | | 607/104 |
| 6,551,348 B1 | 4/2003 | Blalock | |
| 6,572,621 B1 * | 6/2003 | Zheng | A61H 9/0078 |
| | | | 601/152 |
| 6,695,872 B2 | 2/2004 | Elkins | |
| 7,107,629 B2 | 9/2006 | Miros | |
| 7,198,093 B1 | 4/2007 | Elkins | |
| 7,306,568 B2 | 12/2007 | Diana | |
| 7,810,519 B2 | 10/2010 | Tesluk | |
| 7,837,638 B2 | 11/2010 | Miros | |
| 7,896,910 B2 | 3/2011 | Schirrmacher | |
| 8,043,242 B2 | 10/2011 | McSpadden | |
| 8,167,922 B2 | 5/2012 | Ko | |
| 8,182,521 B2 | 5/2012 | Kane | |
| 8,216,290 B2 | 7/2012 | Shawver | |
| 8,282,587 B2 | 10/2012 | McSpadden | |
| 8,444,581 B1 | 5/2013 | Maxon-Maldonado | |
| 8,579,841 B2 * | 11/2013 | Khan | A61H 9/0078 |
| | | | 601/149 |
| 8,597,217 B2 | 12/2013 | Lowe | |
| 8,715,330 B2 | 5/2014 | Lowe | |
| 8,753,383 B2 | 6/2014 | Parish | |
| 8,778,005 B2 | 7/2014 | Parish | |
| 8,827,935 B2 | 9/2014 | Maxon-Maldonado | |
| 8,834,393 B2 | 9/2014 | Maxon-Maldonado | |
| 8,979,915 B2 | 3/2015 | Wilford | |
| 9,114,055 B2 | 8/2015 | Edelman | |
| 9,119,705 B2 | 9/2015 | Parish | |
| 9,180,041 B2 | 11/2015 | Parish | |
| 9,192,539 B2 | 11/2015 | Parish | |
| 9,402,763 B2 | 8/2016 | Bledsoe | |
| 9,433,525 B2 | 9/2016 | Parish | |
| 9,545,286 B2 * | 1/2017 | Rose | F28F 13/10 |
| 9,615,967 B2 | 4/2017 | Lowe | |
| 9,907,692 B2 * | 3/2018 | Binversie | A61N 1/0456 |
| 2001/0039439 A1 * | 11/2001 | Elkins | A61F 7/10 |
| | | | 607/104 |
| 2005/0143797 A1 | 6/2005 | Parish | |
| 2010/0139294 A1 | 6/2010 | Lowe | |
| 2010/0145421 A1 | 6/2010 | Tomlinson | |
| 2011/0307038 A1 | 12/2011 | Stiehr | |
| 2013/0006154 A1 | 1/2013 | Lowe | |
| 2013/0006335 A1 | 1/2013 | Lowe | |
| 2013/0012847 A1 | 1/2013 | Lowe | |
| 2013/0013033 A1 | 1/2013 | Lowe | |
| 2013/0245729 A1 | 9/2013 | Edelman | |
| 2014/0222121 A1 * | 8/2014 | Spence | A61F 7/02 |
| | | | 607/104 |
| 2015/0328042 A1 | 11/2015 | Parish | |

\* cited by examiner

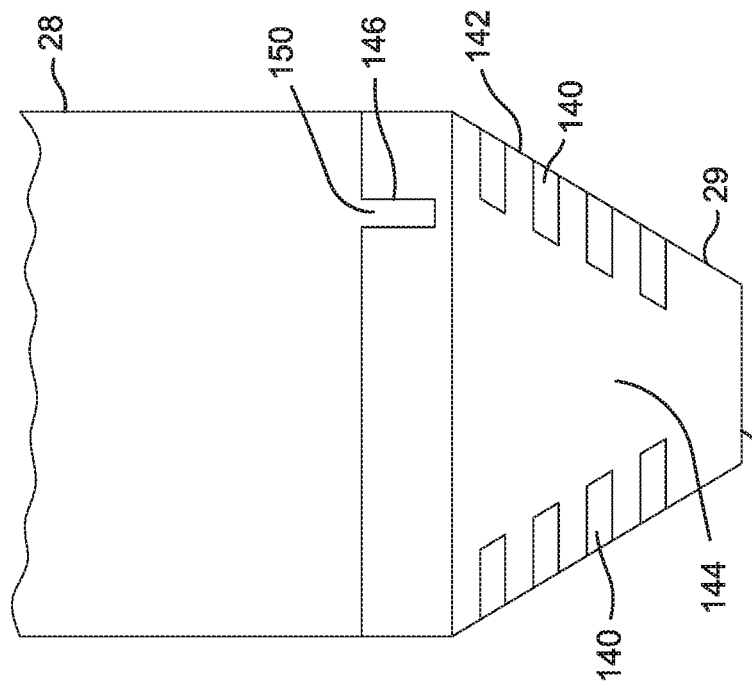
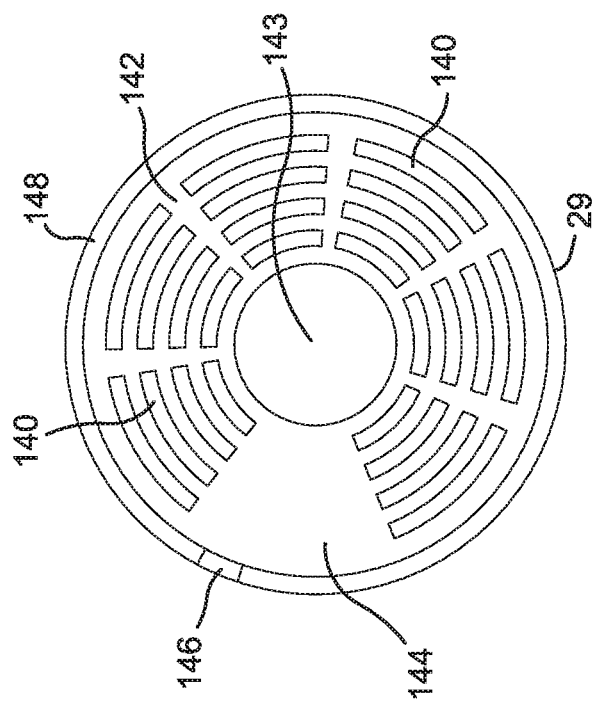

INTEGRATED COLD THERAPY-COMPRESSION THERAPY ASSEMBLY AND ASSOCIATED TREATMENT PROTOCOLS

CROSS-REFERENCE TO RELATED APPLICATIONS

This is a non-provisional patent application claiming the priority of U.S. Provisional Patent Application No. 62/818,091 to Michael G. Johnson et. al. filed on Mar. 13, 2019 which is incorporated herein by reference.

BACKGROUND OF THE INVENTION

The present invention relates generally to medical devices, and more particularly to an integrated assembly or to separate medical devices for applying cold therapy and/or compression therapy to a patient via associated treatment protocols.

Cold therapy devices and compression therapy devices are known in the art. In addition devices are known in the art that integrate the cold therapy function of a cold therapy device and the compression therapy function of a compression therapy device into a single device that performs both functions in an integrated fashion, e.g., the device disclosed in U.S. Pat. No. 9,114,055 to Edelman et. al. which is incorporated herein by reference. However, many integrated cold therapy-compression therapy devices have structural and/or operational shortcomings.

The present invention recognizes the need for an improved therapeutic device that structurally and operationally integrates cold therapy and compression therapy into a single device. Accordingly, it is generally an object of the present invention to provide an integrated cold therapy-compression therapy assembly that has both an effective cold therapy function and an effective compression therapy function. It is more particularly an object of the present invention to provide such an integrated cold therapy-compression therapy assembly, wherein the cold therapy components and compression therapy components of the integrated cold therapy-compression therapy assembly exhibit a structural and operational synergy that complements one another. It is still further an object of the present invention to provide such an integrated cold therapy-compression therapy assembly that overcomes the shortcomings of corresponding prior art devices.

The present invention further recognizes the need for improved therapeutic medical devices that provide cold therapy or compression therapy in separate devices. Accordingly, it is generally an object of the present invention to provide improved therapeutic medical devices that have either an effective cold therapy function or an effective compression therapy function. These objects and others are accomplished in accordance with the invention described hereafter.

SUMMARY OF THE INVENTION

In accordance with one embodiment, the present invention is broadly characterized as an electrically powered, processor-controlled, multi-modality assembly. The assembly is more particularly a single integrated cold therapy-compression therapy assembly that combines a cold therapy module designed to apply cold therapy in a continuous mode and a compression therapy module designed to apply compression therapy in an intermittent mode to select body parts of a user in accordance with associated integrated therapeutic treatment protocols. The body part selected for therapy is dependent on the particular needs of the user. Although the selected body part is oftentimes the knee, the body part selected for therapy using the integrated cold therapy-compression therapy assembly may alternately be, for example, the back, shoulder, hip or foot/ankle.

The integrated cold therapy-compression therapy assembly is intended to be used under the direction of licensed healthcare professionals in hospitals, outpatient clinics, athletic training settings or home settings. The cold therapy module and compression therapy module of the integrated cold therapy-compression therapy assembly each have multiple predetermined operational settings that the user can select for automated modes of therapy. These cold therapy and compression therapy modes can be performed simultaneously or separately from of one another using the integrated cold therapy-compression therapy assembly. The cold therapy mode of operation automatically regulates the temperature of the treatment pad by automatically controlling the proportionate volume of warmed reservoir coolant mixed with cold reservoir coolant entering the coolant pump via the coolant pump inlet. In particular, warmed reservoir coolant returning from the treatment pad to the coolant reservoir is diverted toward the coolant pump inlet where it mixes in an automatically controlled proportion with the cold reservoir coolant from the primary volume of cold coolant in the treatment reservoir.

In accordance with another embodiment, the present invention is characterized as a cold therapy device including a coolant reservoir, a coolant pump and a treatment pad. The coolant reservoir is configured to contain a cold reservoir coolant at a cold reservoir coolant temperature. The coolant pump has a coolant pump inlet and a coolant pump outlet. The coolant pump inlet is submersible in the cold reservoir coolant within the coolant reservoir. The treatment pad has a coolant inlet port, a coolant outlet port and a pad flowpath wending through the treatment pad between the coolant inlet and outlet ports. A coolant discharge is positioned in the coolant reservoir adjacent to the coolant pump inlet and opening into the coolant reservoir. The coolant discharge enables discharge of a warmed reservoir coolant at a warmed coolant outlet temperature into the cold reservoir coolant.

A coolant outlet line is connected to the coolant outlet port and the coolant discharge and a coolant inlet line is connected to the coolant pump outlet and the coolant inlet port. A warmed reservoir coolant flowpath extends from the pad flowpath through the coolant outlet port, the coolant outlet line and the coolant discharge to the coolant reservoir, thereby enabling flow of the warmed reservoir coolant from the pad flowpath to the coolant reservoir. A coolant inlet mixture flowpath extends from the coolant pump inlet through the coolant pump, the coolant pump outlet, the coolant inlet line and the coolant inlet port to the pad flowpath, thereby enabling flow of a coolant inlet mixture from the coolant reservoir to the pad flowpath. The coolant inlet mixture contains the warmed reservoir coolant from the coolant discharge and the cold reservoir coolant from the coolant reservoir. The coolant inlet mixture has a coolant inlet mixture temperature and a coolant inlet ratio defined by relative proportions of the warmed reservoir coolant and the cold reservoir coolant in the coolant inlet mixture.

A cover encloses a reservoir coolant mixing chamber having the coolant pump inlet and the coolant discharge positioned therein. The cover is submersible in the cold reservoir coolant within the coolant reservoir. The cover has a plurality of coolant openings formed therein enabling reservoir coolant to pass between the coolant reservoir external to the cover and the reservoir coolant mixing chamber. A diverter panel is provided in the cover. The diverter panel is continuously fluid-impermeable and free of any coolant openings. The diverter panel is positioned adjacent to the coolant discharge and oriented relative to the coolant discharge and the coolant pump inlet such that the warmed reservoir coolant dispersing from the coolant discharge in a direction away from coolant pump inlet is redirected in an opposing direction back toward the coolant pump inlet by the diverter panel.

The cold therapy device may additionally include a microprocessor and a coolant reservoir return line. The microprocessor controls operation of the coolant pump. The coolant reservoir return line has an open end which is the coolant discharge. The cold therapy device may also additionally include an inlet coolant manifold connecting the coolant pump outlet to the coolant inlet line, an outlet coolant manifold connecting the coolant outlet line to the coolant reservoir return line at another end of the coolant reservoir return line opposite the open end, a coolant pressure relief valve connected to the inlet coolant manifold and a pressure relief valve recirculation loop extending between the coolant pressure relief valve and the outlet coolant manifold. The pressure relief valve recirculation loop and coolant pressure relief valve when open provide a bleed coolant flowpath between the inlet and outlet coolant manifolds. The coolant reservoir may also include a reservoir container and a reservoir lid. The reservoir container has a reservoir opening that is selectively covered or uncovered by the reservoir lid. The reservoir lid has a portion housing the coolant pump and this same portion has the cover attached thereto.

In accordance with another embodiment, the present invention is characterized as a cold therapy treatment method. A cold reservoir coolant is mixed with a warmed reservoir coolant in a reservoir coolant mixing chamber to form a coolant inlet mixture having a coolant inlet mixture temperature. The coolant inlet mixture may have a coolant inlet ratio of the warmed reservoir water to the cold reservoir water in a range between about 1:4 and about 1:10. The reservoir coolant mixing chamber is enclosed in a cover and has a coolant pump inlet and a coolant discharge positioned therein. The reservoir coolant mixing chamber is positioned within a reservoir container containing the cold reservoir coolant and is submersed in the cold reservoir coolant. The cold reservoir coolant has a cold reservoir coolant temperature and the warmed reservoir coolant has a warmed coolant outlet temperature higher than the cold reservoir coolant temperature. The coolant inlet mixture temperature is between the warmed coolant outlet temperature and the cold reservoir coolant temperature.

The coolant inlet mixture is drawn into a coolant pump from the reservoir coolant mixing chamber via the coolant pump inlet. The coolant inlet mixture is conveyed from the coolant pump through a pump outlet, a coolant inlet line and a coolant inlet port into a coolant compartment in a treatment pad mounted on a body of a user. The treatment pad has a treatment pad temperature dependent at least in part on the coolant inlet mixture temperature. The coolant inlet mixture is conveyed into the coolant compartment by means of the coolant pump operating at a coolant pump speed. The coolant inlet mixture is then conveyed along a pad flowpath in the coolant compartment that wends from the coolant inlet port to a coolant outlet port. The coolant inlet mixture is warmed in the pad flowpath by means of heat transfer with the body to form the warmed reservoir coolant.

The warmed reservoir coolant is conveyed from the pad flowpath into the reservoir coolant mixing chamber via a coolant outlet line and the coolant discharge. The cold reservoir coolant flows into the reservoir coolant mixing chamber from a primary volume of reservoir coolant in the reservoir container external to the cover through a plurality of coolant openings formed in a perforated panel of the cover. The cover has also a diverter panel free of any coolant openings, thereby preventing flow of any reservoir coolant in either direction therethrough. The diverter panel is positioned adjacent to the coolant discharge and oriented relative to the coolant discharge and the coolant pump inlet such that the warmed reservoir coolant dispersed from the coolant discharge in a direction away from the coolant pump inlet is redirected in an opposing direction back toward the coolant pump inlet by the diverter panel. The above method may alternately be practiced in the same manner as described above, but with the coolant pump operating at a slower pump speed to increase the treatment pad temperature.

In accordance with another embodiment, the present invention is characterized as a compression therapy device including a compressant pump, a treatment pad, a compressant inlet/outlet line, a compressant inlet flowpath, a solenoid vent, a compressant outlet flowpath and a microprocessor. The compressant pump has a compressant pump inlet and a compressant pump outlet line. The treatment pad has a compressant compartment and a compressant inlet/outlet port opening into the compressant compartment. The compressant inlet/outlet line is connected to the inlet/outlet compressant port. The compressant manifold connects the compressant inlet/outlet line and the compressant pump outlet line to one another. The compressant inlet flowpath includes the compressant pump, compressant pump outlet line, compressant inlet/outlet line and compressant inlet/outlet port. The compressant inlet flowpath extends between the compressant pump inlet and the compressant compartment of the treatment pad.

The solenoid vent has a biased open position and a closed position. The solenoid vent may be positioned at the compressant manifold. The solenoid vent is in the compressant inlet flowpath when in the closed position, thereby retaining a pressurized compressant in the compressant compartment. The compressant outlet flowpath includes the compressant inlet/outlet port and the compressant inlet/outlet line. The compressant outlet flowpath extends between the solenoid vent and the compressant compartment of the treatment pad. The solenoid vent is in the compressant outlet flowpath when in the biased open position, thereby venting the pressurized compressant in the compressant compartment from the compressant outlet flowpath. The microprocessor controls operation of the compressant pump and solenoid valve.

The compression therapy device may further include a pressure transducer and a communication link between the pressure transducer and the microprocessor. The pressure transducer is in fluid communication with the compressant inlet and outlet flowpaths to determine a compressant pressure therein.

In accordance with another embodiment, the present invention is characterized as a compression therapy treatment method. A solenoid vent in a compressant inlet flowpath is activated to close the solenoid vent. An inflation stage is initiated by activating a compressant pump to pressurize an ambient compressant received into the compressant pump via a compressant pump inlet, thereby transforming the ambient compressant to a pressurized compressant. The compressant pump is operated at an inflation stage output level to convey the pressurized compressant from the compressant pump via the compressant inlet flowpath to a compressant compartment in a treatment pad. The compressant inlet flowpath includes a compressant pump outlet line, a compressant inlet/outlet line and a compressant inlet/outlet port opening into the compressant compartment. Compressant pressure in the compressant inlet flowpath and correspondingly in the compressant compartment is monitored with a pressure transducer and a microprocessor in communication with one another. The pressure transducer is in fluid communication with the compressant inlet flowpath.

The inflation stage is terminated and a hold stage is simultaneously initiated when the pressure transducer detects a predetermined peak pad pressure in the compressant compartment. The hold stage is initiated by maintaining the solenoid vent in the closed position, but reducing the output level of the compressant pump to a lower hold stage output level sufficient to maintain pad pressure in the compressant compartment at the peak pad pressure without increasing pad pressure above the peak pad pressure. The time duration of the hold stage is monitored and the hold stage is terminated and a deflation stage is simultaneously initiated when a predetermined hold time expires. The deflation stage is initiated by inactivating the compressant pump and inactivating the solenoid vent, thereby transitioning the solenoid vent from the closed position to the biased open position. The pressurized compressant in the compressant compartment flows through a compressant outlet flowpath to the solenoid vent that is biased in the open position. The compressant outlet flowpath includes the inlet/outlet port and the compressant inlet/outlet line, but excludes the compressant pump outlet line. The pressurized compressant is discharged from the compressant outlet flowpath through the solenoid vent.

The compressant pressure in the compressant outlet flowpath and correspondingly in the compressant compartment is monitored with the microprocessor and the pressure transducer. The deflation stage is terminated and a dwell stage is simultaneously initiated when the pressure transducer detects a predetermined minimum pad pressure in the compressant compartment. The dwell stage is initiated by maintaining the solenoid vent in the closed position and the compressant pump inactive to maintain the minimum pad pressure in the compressant compartment. The time duration of the dwell stage is monitored and the dwell stage is terminated when a predetermined dwell time expires. The inflation stage may simultaneously be initiated anew when the dwell stage is terminated and thereafter repeating the hold, deflation and dwell stages. The above method may alternately be practiced in the same manner as described above, but wherein the predetermined peak pad pressure is reduced.

In accordance with another embodiment, the present invention is characterized as an integrated cold therapy-compression therapy assembly including a cold therapy module and a compression therapy module substantially similar to the above-described cold therapy device and compression therapy device described above. The coolant reservoir of the integrated assembly may include a reservoir container and reservoir lid. The reservoir container is configured to retain the cold reservoir coolant and has a reservoir opening surrounded by a rim defining an opening shape and dimensions. The reservoir lid is configured to selectively cover or uncover the reservoir opening. The reservoir lid has an upper portion and a lower portion. The upper portion has an outer top face, an inner bottom face and an upper portion perimeter with a perimeter shape and dimensions in correspondence with the opening shape and dimensions, thereby enabling the upper portion perimeter to closely engage the rim when the reservoir lid selectively covers the reservoir opening.

The lower portion has a top end, a bottom end and an elongate shape that is narrower relative to the upper portion perimeter. The top end of the lower portion is integral with the inner bottom face of the upper portion and the lower portion extends away from the upper portion. The cover is fitted onto the bottom end of the lower portion and the lower portion houses the coolant pump, the coolant pump inlet, a lower segment of the coolant pump outlet and the coolant discharge. The upper portion of the reservoir lid houses an upper segment of the coolant pump outlet, an internal segment of the coolant inlet line, an internal segment of the coolant outlet line, the compressant pump inlet, the compressant pump, the compressant pump outlet line, the compressant manifold, the solenoid vent, an internal segment of the compressant inlet/outlet line and the shared microprocessor. The upper portion is sealed against liquid intrusion from the lower portion or from outside the reservoir lid except for reservoir coolant passing through the upper portion while fully contained within the coolant pump outlet and the coolant inlet and outlet lines. The integrated assembly may also include a control panel having a user input/output mounted on the outer top face of the upper portion of the reservoir lid.

The present invention will be further understood from the drawings and the following detailed description.

BRIEF DESCRIPTION OF THE SEVERAL VIEWS OF THE DRAWINGS

The below-listed drawing figures illustrate one or more embodiments of the present invention by way of example and not by way of limitation. Common reference characters may be used among the different drawing figures to indicate the same or similar structural elements.

FIG. 15 is a top plan view into the interior of a coolant port cover that is mountable on the bottom of the reservoir lid.

FIG. 16 is a side elevation view of the coolant port cover of FIG. 15 rotated 90° counter-clockwise and mounted on the bottom of the reservoir lid.

DESCRIPTION OF PREFERRED EMBODIMENT(S)

Figure 1:
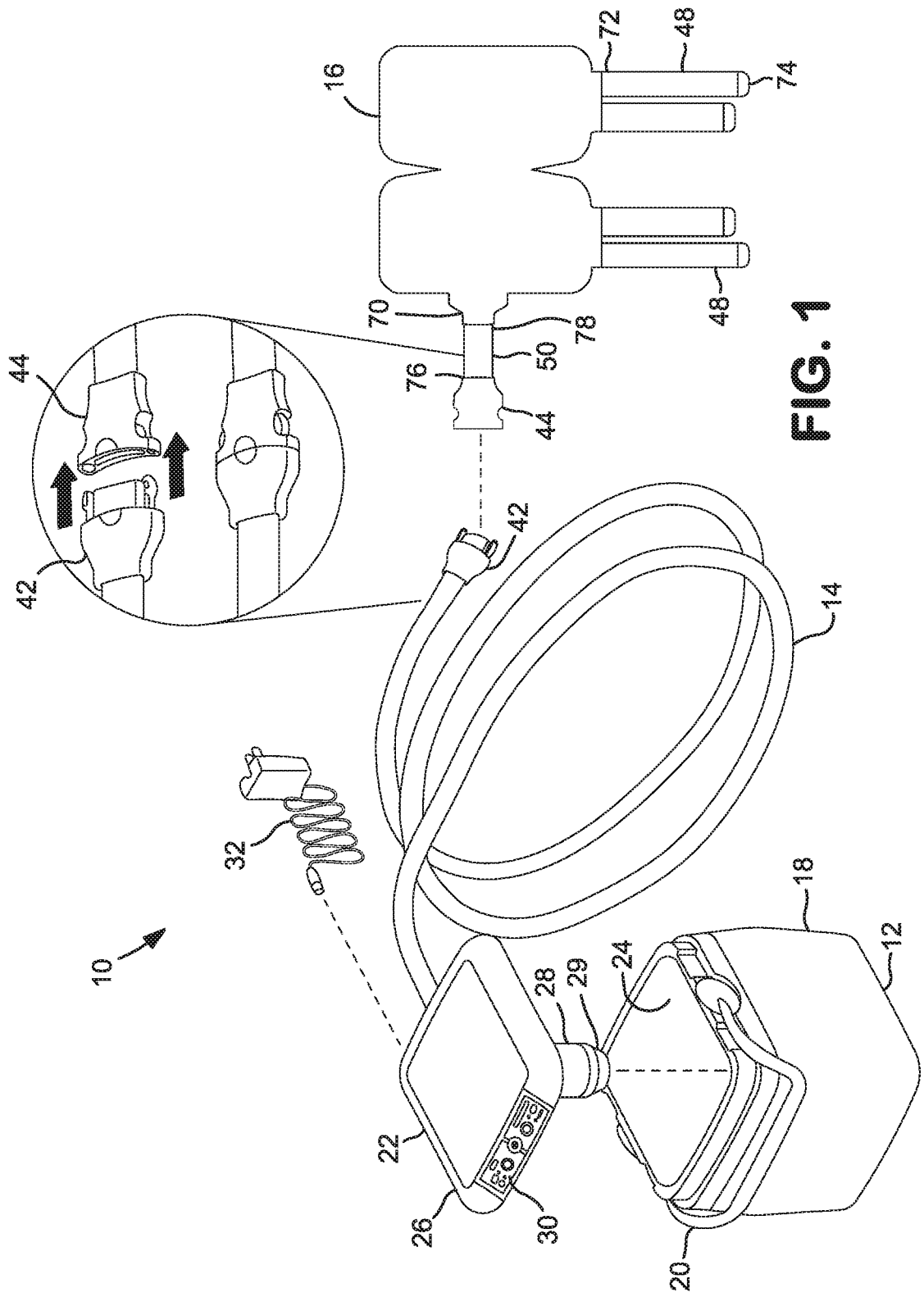
FIG. 1 is a view of an embodiment of an integrated cold therapy-compression therapy assembly in a disassembled condition.
Figure 2:
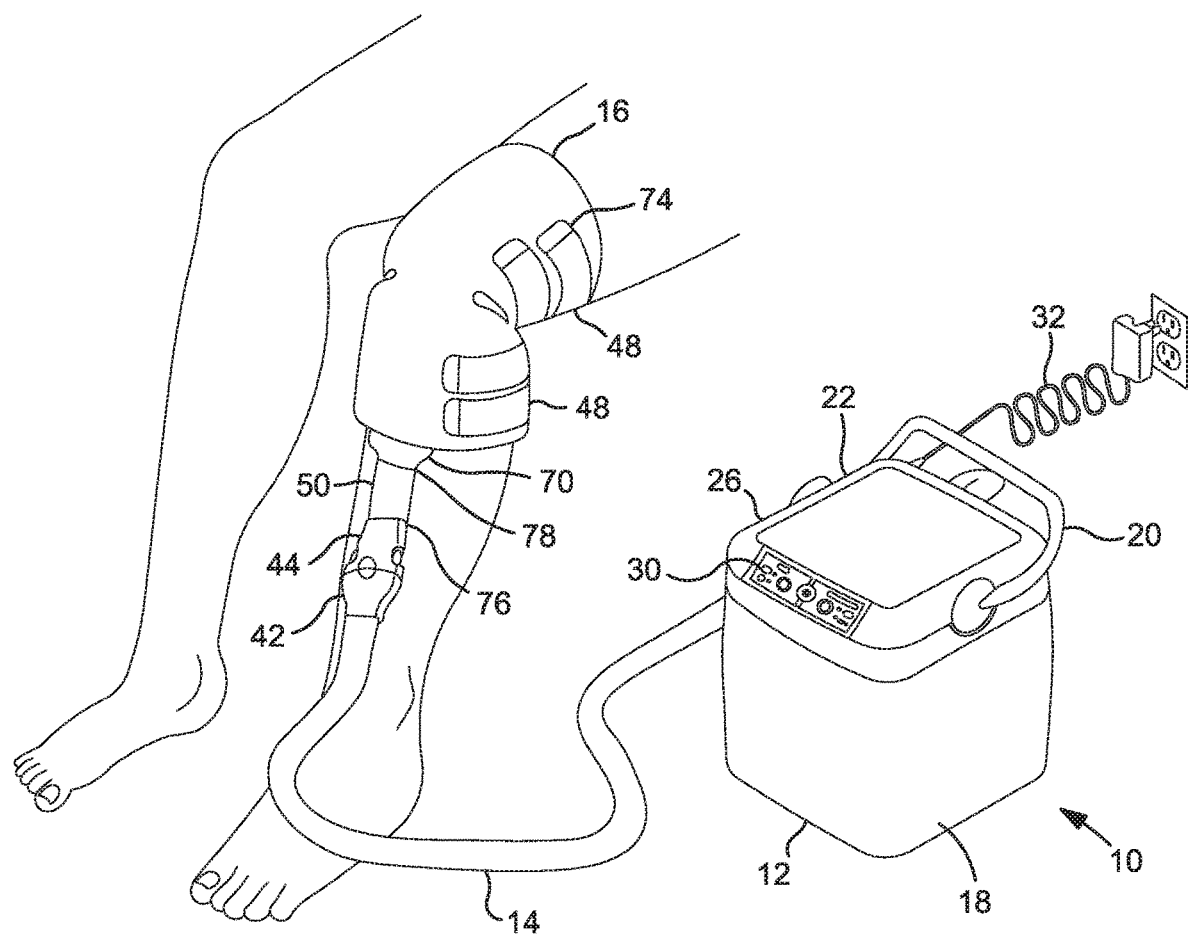
FIG. 2 is a view of the integrated cold therapy-compression therapy assembly of FIG. 1 in a fully assembled condition having a treatment pad applied to the knee of a user.

An embodiment of an integrated cold therapy-compression therapy assembly generally designated 10 is shown in FIG. 1 in a disassembled condition and is shown in FIG. 2 in a fully assembled condition. When charged with a coolant and fully assembled, the integrated cold therapy-compression therapy assembly 10 has utility for the application of cold therapy and/or compression therapy to a patient via associated treatment protocols. With reference to FIGS. 1 and 2, the integrated cold therapy-compression therapy assembly 10 comprises a coolant reservoir 12, a tubing bundle 14 and a treatment pad 16.

Figure 3:
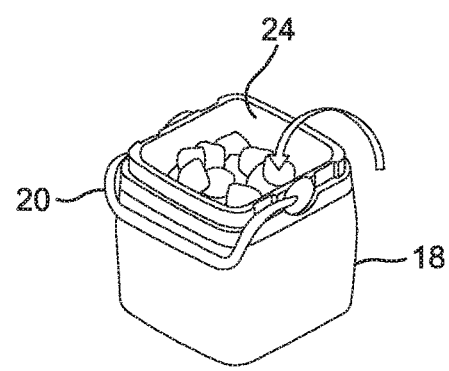
FIG. 3 is a perspective view of a coolant reservoir having utility in the integrated cold therapy-compression therapy assembly of FIG. 1, wherein a reservoir lid has been removed from the top of the coolant reservoir to charge the coolant reservoir with a coolant.

The coolant reservoir 12 is preferably constructed from a rigid and durable material such as a high-strength plastic that is fluid impervious. The coolant reservoir 12 includes a reservoir container 18, a reservoir handle 20 and a reservoir lid 22. The reservoir container 18 resembles the body of a conventional hard-sided picnic cooler and as such is preferably configured in the shape of a six-sided cube or more generally a rectangular cuboid having a fully-enclosed bottom side, four fully-enclosed continuous upright sides and a top side with a reservoir opening 24 spanning the entire top side. The reservoir opening 24 enables access to the hollow interior of the reservoir container 18 from the outside and has specific utility for charging the coolant reservoir 12 with a coolant as shown in FIG. 3. A preferred coolant is a fluid chilled below ambient temperature, a more preferred coolant is a chilled liquid such as chilled water and a most preferred coolant is ice water approaching the freezing point of water. In addition to the coolant, the coolant reservoir 12 may also be charged with a solid passive cooling medium such as a cold pack containing a frozen liquid or gel or simply loose ice as shown in FIG. 3. The bottom and upright sides of the reservoir container 18 are fluid impervious and are preferably insulated, thereby enabling the interior of the reservoir container 18 to retain the coolant in a chilled state therein. The reservoir handle 20 is rotatably attached to the reservoir container 18 and assists a user in carrying the coolant reservoir 12.

The reservoir lid 22 is configured and sized to cover the entirety of the reservoir opening 24 and fit snugly against the top edges of the four upright sides that form the outer rim of the reservoir opening 24. When the reservoir lid 22 is snugly fitted atop the reservoir opening 24, the reservoir lid 22 in cooperation with the bottom and upright sides of the reservoir container 18 facilitates temperature maintenance of the coolant retained in the interior of the reservoir container 18. The reservoir lid 22 preferably additionally functions as a unitary housing for mechanical and electronic components of the integrated cold therapy-compression therapy assembly 10 that enable its operation.

The reservoir lid 22 has a first or upper portion 26 and a second or lower portion 28, both of which function inter alia as hollow housings for internal operational components of the integrated cold therapy-compression therapy assembly 10 as shown and described in detail hereafter. The upper portion 26 has an outer top face, an inner bottom face, a perimeter defined by the edges of the faces and a low side profile. The outer top face is relatively flat and the perimeter is shaped and dimensioned in correspondence with the shape and dimensions of the reservoir opening 24 (typically square or rectangular) so that the perimeter closely engages the rim of the reservoir opening 24 when the reservoir lid 22 is atop the reservoir opening 24 and closes off the reservoir opening 24 from the outside. The lower portion 28 of the reservoir lid 22 has a top end, a bottom end and an elongate cylindrical shape that is narrow relative to the perimeter of the upper portion 26. The top end is integral with the inner bottom face of the upper portion 26 and the lower portion 28 extends away from the upper portion 26 to the bottom end of the lower portion 28 which has a perforated bottom cover 29 press-fitted onto it.

A control panel 30 is mounted in the exterior face of the reservoir lid 22. The control panel 30 includes input keys and output displays which are used to control operation of the integrated cold therapy-compression therapy assembly 10 and enable the user to select different predetermined treatment protocols under the direction of a healthcare professional. Further details of the control panel 30 are described below. The integrated cold therapy-compression therapy assembly 10 further comprises an assembly power line 32 that supplies electric power from a remote power source to the internal operational components housed in the reservoir lid 22. A preferred assembly power line 32 is a conventional electrical power cord having a two or three-prong male plug and an AC to DC power converter at one end and a single-prong male plug at the other end. The two or three-prong male plug and power converter are connectable to an electrical outlet carrying standard household AC and the single-prong plug is connectable to a power jack (shown and described below with reference to FIG. 7) at the reservoir lid 22.

Figure 4:
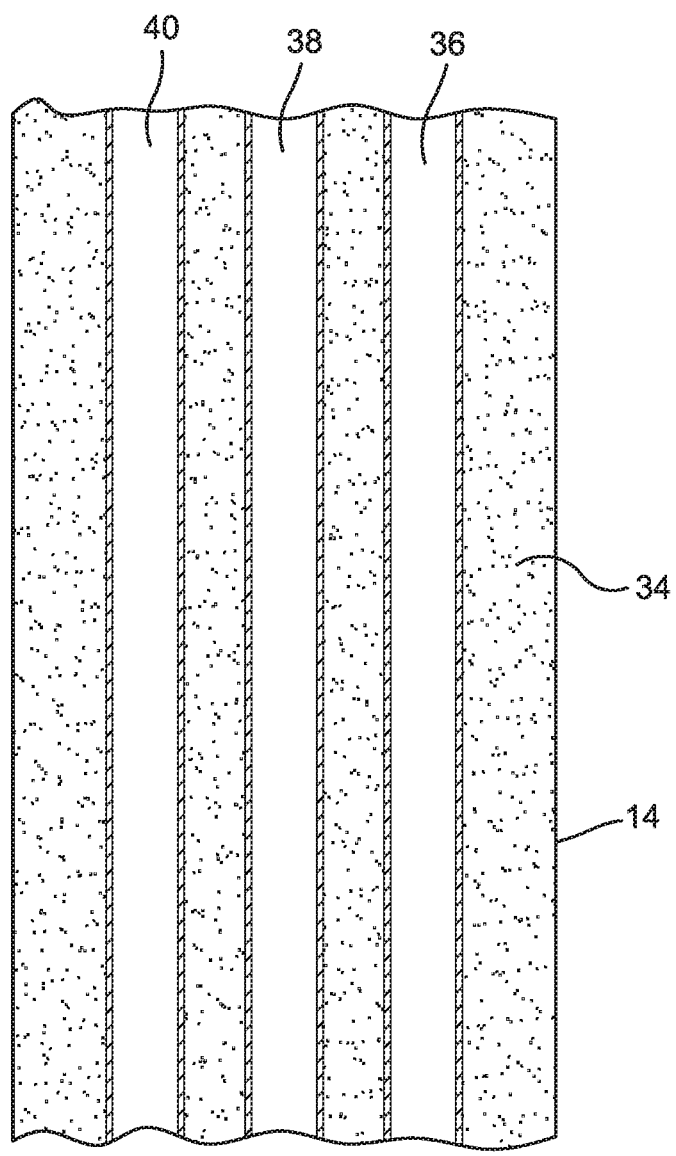
FIG. 4 is a cross section of a tubing bundle having utility in the integrated cold therapy-compression therapy assembly of FIG. 1.

Referring additionally to FIG. 4, the tubing bundle 14 includes a continuous sheath 34 that surrounds and encloses a coolant inlet line 36, a coolant outlet line 38 and a compressant inlet/outlet line 40. The sheath 34 preferably has a smooth external surface and is formed from a pliant insulative material such as a foam. Each fluid line 36, 38, 40 has the configuration of a pliant fluid-impervious hollow tube with two ends. The first or proximal end of each fluid line 36, 38, 40 extends into the interior of the reservoir lid 22 and the second or distal ends of the fluid lines 36, 38, 40 are jointly fitted with a shared first coupling element 42. The term "proximal" as used here refers to the relative positioning of structural elements with respect to the reservoir lid 22. A corresponding shared second coupling element 44 is fitted to the treatment pad 16. The first coupling element 42 is a male fixture and the second coupling element 44 is a female fixture that are selectively attachable to and releasable from one another. It is understood that the configurations of the first and second coupling elements 42, 44 may be reversed such that the first coupling element 42 is a female fixture and the second coupling element 44 is a male fixture. In any case, the first and second coupling elements 42, 44 in combination form a pad coupler. The pad coupler 42, 44 enables selective attachment of the fluid lines 36, 38, 40 to the treatment pad 16, thereby providing fluid communication between the treatment pad 16 and the coolant reservoir 12 including the internal operational components housed in the reservoir lid 22.

In addition to the second coupling element 44, the treatment pad 16 includes a bladder 46, a plurality of retention straps 48 and a tubing bundle stub 50. The bladder 46 forms the main body of the treatment pad 16 and has a unitary construction somewhat similar to the bladders disclosed in the cold therapy treatment pads of U.S. Pat. Nos. 7,914,563 and 9,170,059 both of which are incorporated herein by reference. The bladders taught in the recited patents are each constructed by positioning two like-sized sheets of a flexible, fluid impermeable material side by side and continuously bonding them together along their abutting peripheral edges. The resulting space between the peripherally bonded sheets defines a fluid compartment in the interior of the bladder. Inlet and outlet ports are also provided through the bonded peripheral edges for fluid to flow into and out of the interior fluid compartment.

Figure 5:
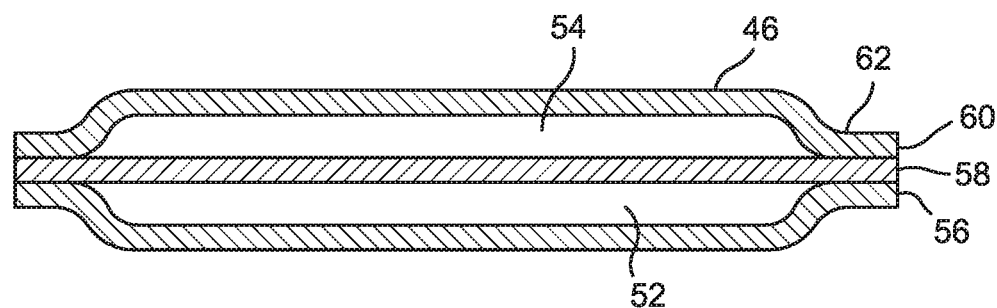
FIG. 5 is a cross section of a dual-compartment bladder taken along line 5-5 which has utility in the integrated cold therapy-compression therapy assembly of FIG. 1.

Unlike the bladders disclosed in the two patents cited above which enclose a single fluid compartment and receive a single treatment fluid, the bladder 46 of the treatment pad 16 (described hereafter with added reference to FIGS. 5 and 6) encloses two separate, but abutting and coextensive, fluid compartments, i.e., a compressant compartment 52 and a coolant compartment 54, which are in fluid isolation from one another. The compressant compartment 52 receives the compressant and the coolant compartment 54 separately receives the coolant during operation of the integrated cold therapy-compression therapy assembly 10. The unitary dual-compartment bladder 46 is constructed from three like-sized sheets of flexible, fluid impermeable material. In particular, a front sheet 56, a middle sheet 58 and a back sheet 60 are positioned side by side and continuously bonded together along their abutting peripheral edges 62. Bonding the front and middle sheets 56, 58 at their abutting peripheral edges 62 creates the compressant compartment 52 in the space between the front and middle sheets 56, 58 that is bordered by the resulting peripheral bond. Bonding the back and middle sheets 60, 58 at their abutting peripheral edges 62 similarly creates the coolant compartment 54 in the space between the back and middle sheets 60, 58 that is likewise bordered by the resulting peripheral bond. A plurality of bladder ports 64, 66, 68 are provided in a portal segment 70 of the bonded peripheral edges 62 of the bladder 46 where the tubing bundle stub 50 intersects and attaches to the bladder 46.

The bladder 46 is pliable even when a treatment fluid resides in one or both of the fluid compartments 52, 54, thereby enabling the bladder 46 to conform to the contours of a user's body when the bladder 46 is applied to a part of the user's body requiring cold therapy and compression therapy, e.g., the knee as shown in FIG. 2. Each retention strap 48 of the treatment pad 16 is preferably constructed from a pliant fabric and has a first or fixed end 72 and a second or free end 74 with a releasable fastener such as a hook and loop fastener affixed thereto. (Note that the retention straps 48 are omitted from FIG. 5 for clarity.) The fixed ends 72 of the retention straps 48 are attached to the bladder 46 and the free ends 74 extend away from the peripheral edges 62 of the bladder 46.

To properly mount the bladder 46 on the user's body, the user places the bladder 46 on the part of the user's body to be treated, e.g., the knee, with the coolant compartment 54 of the bladder 46 positioned immediately next to the user's body and the compressant compartment 52 overlaying the coolant compartment 54 more distal from the user's body than the compressant compartment 52. The user firmly presses the bladder 46 against the part of the user's body to which it is applied so that the bladder 46 bends in conformance with the contours of the respective body part. The user then tightly wraps the retention straps 48 around the body part and releasably fastens the fastener on the free ends 74 to a cooperative fastener (not shown) on the outside back face of the bladder 46, thereby tightly retaining the bladder 46 on the body part to enhance both cold therapy and compression therapy treatment thereof. The retention straps 48 tightly retain the bladder 46 against the user's body and apply a counter-force in the direction of the user's body which desirably opposes the expansion force of the compressant compartment 52 that is directed away from the user's body during compression therapy. Once the treatment pad 16 is properly mounted on the desired body part, the integrated cold therapy-compression therapy assembly 10 may be activated to selectively circulate coolant between the coolant reservoir 12 and coolant compartment 54 of the dual-compartment bladder 46, thereby providing the desired body part with continuous cold therapy in a manner described below. Alternatively or additionally the integrated cold therapy-compression therapy assembly 10 may be activated to selectively cycle the compressant into and out of the compressant compartment 52 of the dual-compartment bladder 46, thereby providing the desired body part with intermittent compression therapy in a manner described below.

The tubing bundle stub 50 has essentially the same construction as the tubing bundle 14, but is significantly shorter in length. As such, the tubing bundle stub 50 includes short extensions of the fluid lines 36, 38, 40 that are enclosed within a short extension of the sheath 34. The tubing bundle stub 50 provides a short flexible tie-in between the bladder 46 and the second coupling element 44. It is preferable to connect the bladder 46 to the second coupling element 44 via the tubing bundle stub 14 rather than directly attaching the second coupling element 44 to the bladder 46 because the second coupling element 44 is rigid. Directly attaching the second coupling element 44 to the bladder 46 could unduly stress the bladder 46 at the attachment point, particularly when positioning or re-positioning the treatment pad 16 on a user's body during use of the integrated cold therapy-compression therapy assembly 10, which would increase the risk that the bladder 46 would fail at the attachment point. Accordingly, the tubing bundle stub 50 diminishes the stress on the bladder 46 when the tubing bundle 14 is displaced while connected to the bladder 46.

Figure 6:
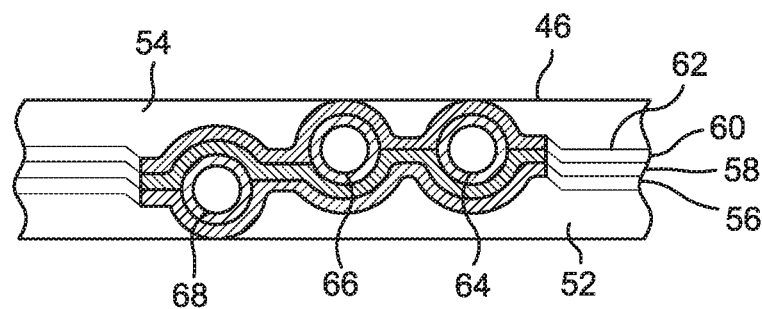
FIG. 6 is a cross section of a portal segment of the dual-compartment bladder taken along line 6-6.

The tubing bundle stub 50 has two ends 76, 78. The first end 76 is a proximal end to which the second coupling element 44 is fixably attached. The terms "proximal" and "distal" as used here refer to the relative positioning of structural elements with respect to the reservoir lid 22 when the pad coupler 42, 44 is engaged. The second end 78 of the tubing bundle stub 50 is a distal end to which the bladder 46, and more particularly the portal segment 70 of the bladder 46, is fixably attached. Referring to FIG. 6, the specific bladder ports provided at the portal segment 70 are the coolant inlet port 64, the coolant outlet port 66 and the compressant inlet/outlet port 68. A preferred coolant inlet port 64 is the distal end of the short extension of the coolant inlet line 36 which opens through the bonded peripheral edges 62 into the coolant compartment 54 and enables the coolant to enter the coolant compartment 54. A preferred coolant outlet port 66 is the distal end of the short extension of the coolant outlet line 36 which also opens through the bonded peripheral edges 62 into the coolant compartment 54 and enables the coolant to exit the coolant compartment 54. A preferred compressant inlet/outlet port 68 is the distal end of the short extension of the compressant inlet/outlet line 40 which opens through the bonded peripheral edges 62 into the compressant compartment 52 and enables a desired compressant to enter and exit the compressant compartment 52. A desired compressant is preferably a gas and more preferably air.

The coolant and compressant compartments 52, 54 are preferably provided with a plurality of spot bonds that, although not shown in the drawings, are similar to the spot bonds disclosed in U.S. Pat. Nos. 7,914,563 and 9,170,059. The spot bonds join the two sheets in each respective compartment 52, 54 to one another at periodically spaced-apart intervals across the span of the compartments 52, 54. The spot bonds prevent over-expansion of the coolant and compressant compartments 52, 54 so that they do not take on an undesirable bulbous shape. In the case of the coolant compartment 54, the spot bonds also advantageously direct the coolant in a tortuous pad flowpath for the coolant through the coolant compartment 54 between the coolant inlet and outlet ports 64, 66 during operation of the integrated cold therapy-compression therapy assembly 10.

Figure 7:
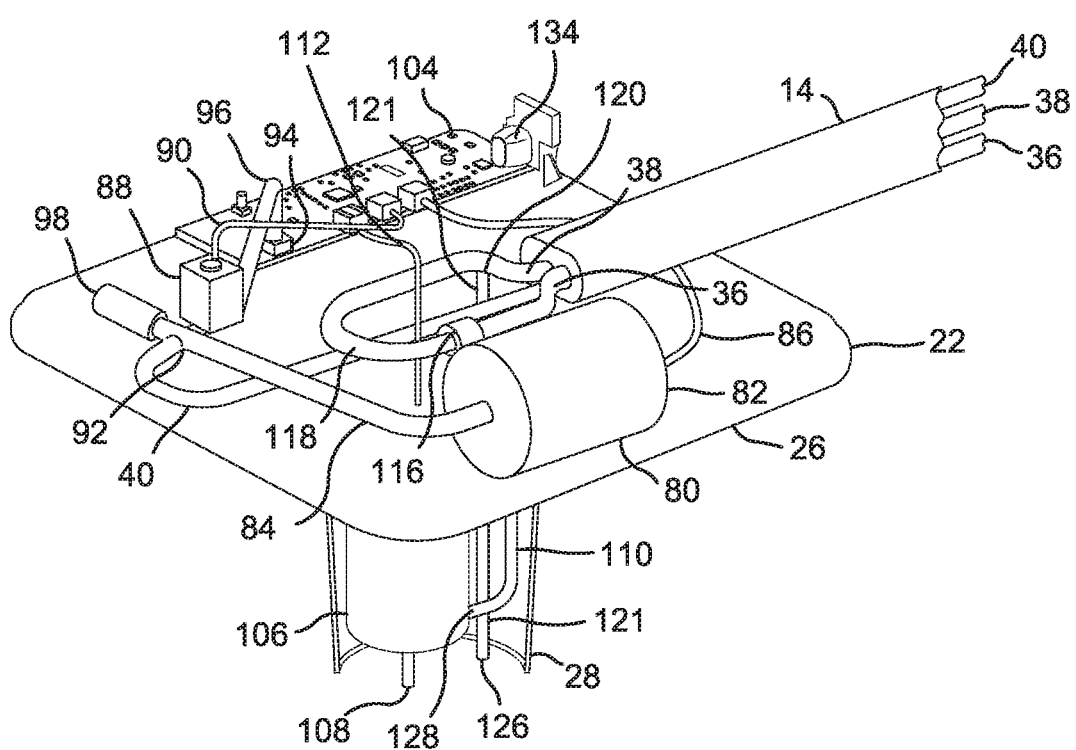
FIG. 7 is a cut-away view of the reservoir lid for the coolant reservoir showing internal operational components of the integrated cold therapy-compression therapy assembly of FIG. 1 housed within the reservoir lid.
Figure 8:
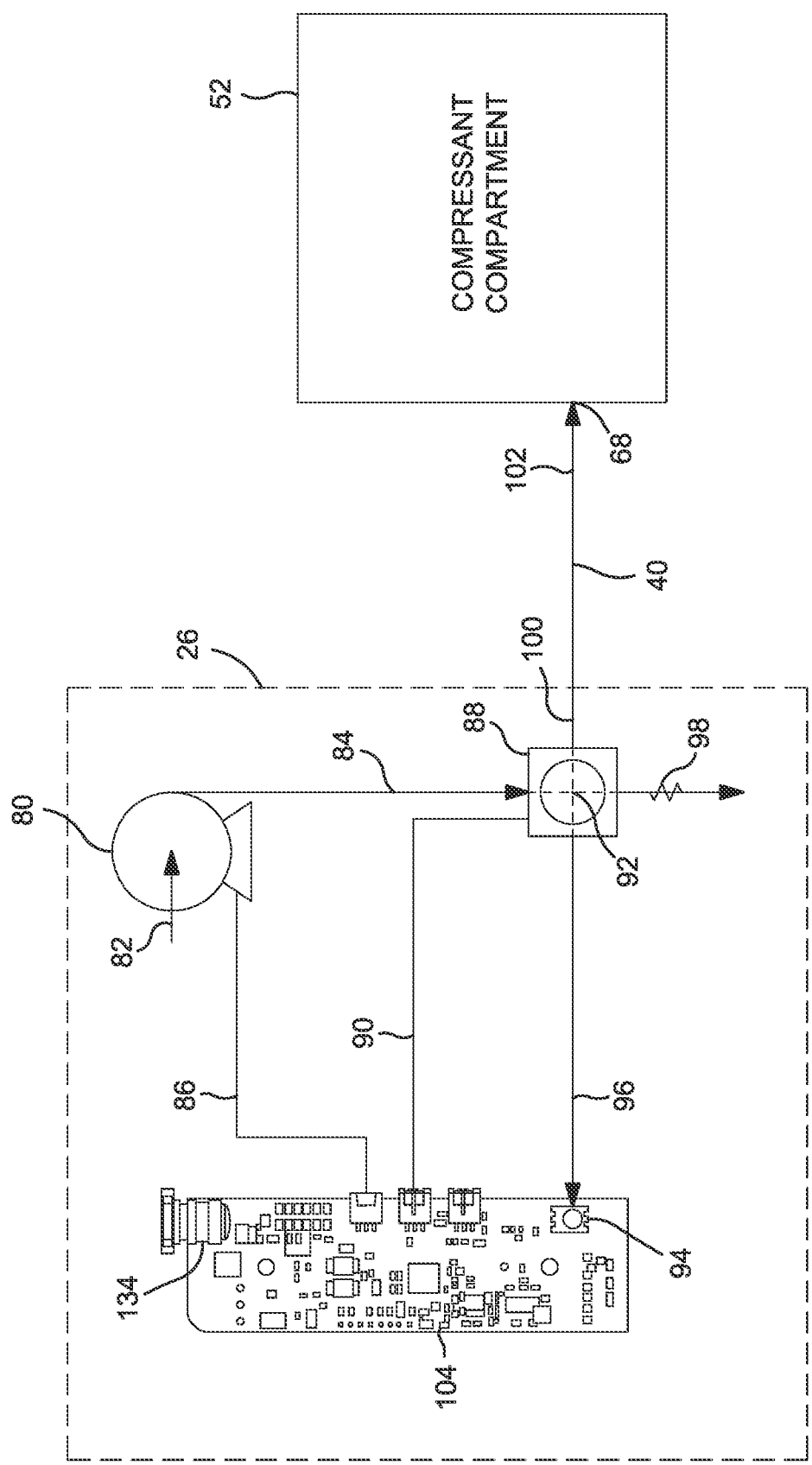
FIG. 8 is a structural schematic of a compression therapy module having utility in the integrated cold therapy-compression therapy assembly of FIG. 1, wherein an air flowpath through the compression therapy module is shown while performing a pad inflation stage of a compression therapy cycle.
Figure 9:
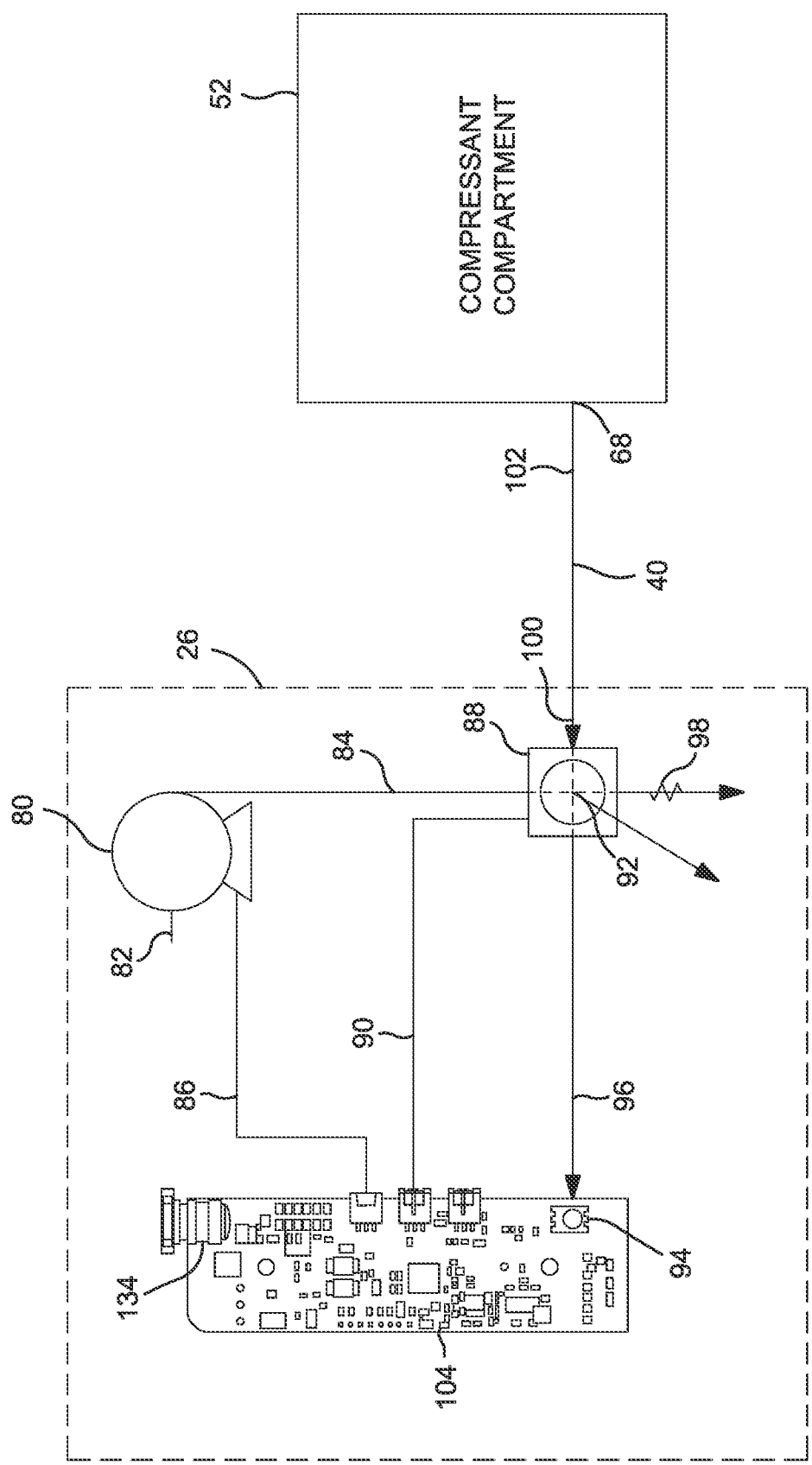
FIG. 9 is the structural schematic of FIG. 8, wherein the air flowpath through the compression therapy module is shown while performing a treatment pad deflation stage of the compression therapy cycle.

Although the cold therapy-compression therapy assembly 10 is a structurally and functionally integrated system, the assembly 10 has two different modes of operation that can be performed simultaneously or separately from one another, namely, 1) a compression therapy mode and 2) a cold therapy mode. Most of the operational components of the integrated cold therapy-compression therapy assembly 10 used to perform these two modes of operation are housed in the reservoir lid 22. Referring to FIGS. 7-9, a compressant pump 80, a compressant pump inlet 82, a compressant pump outlet line 84, a compressant pump power line 86, a compressant solenoid 88, a solenoid power line 90, a compressant manifold 92, a pressure transducer 94, a pressure transducer line 96, a compressant pressure relief valve (PRV) 98 and an internal segment 100 of the compressant inlet/outlet line 40 are among the internal operational components used to perform the compression therapy mode that are housed in the reservoir lid 22. More specifically, these internal operational components are housed in the upper portion 26 of the reservoir lid 22. The above-listed components 80, 82, 84, 86, 88, 90, 92, 94, 96, 98, 100 along with an external segment 102 of the compressant inlet/outlet line 40, the compressant compartment 52 of the bladder 46 and a shared printed circuit board assembly (PCBA) 104 (which is also housed in the upper portion 26 of the reservoir lid 22) make up the compression therapy module of the integrated cold therapy-compression therapy assembly 10. The PCBA 104 has a microprocessor with firmware that inter alia controls operation of the compressant pump 80, compressant solenoid 88 and pressure transducer 94.

Figure 10:
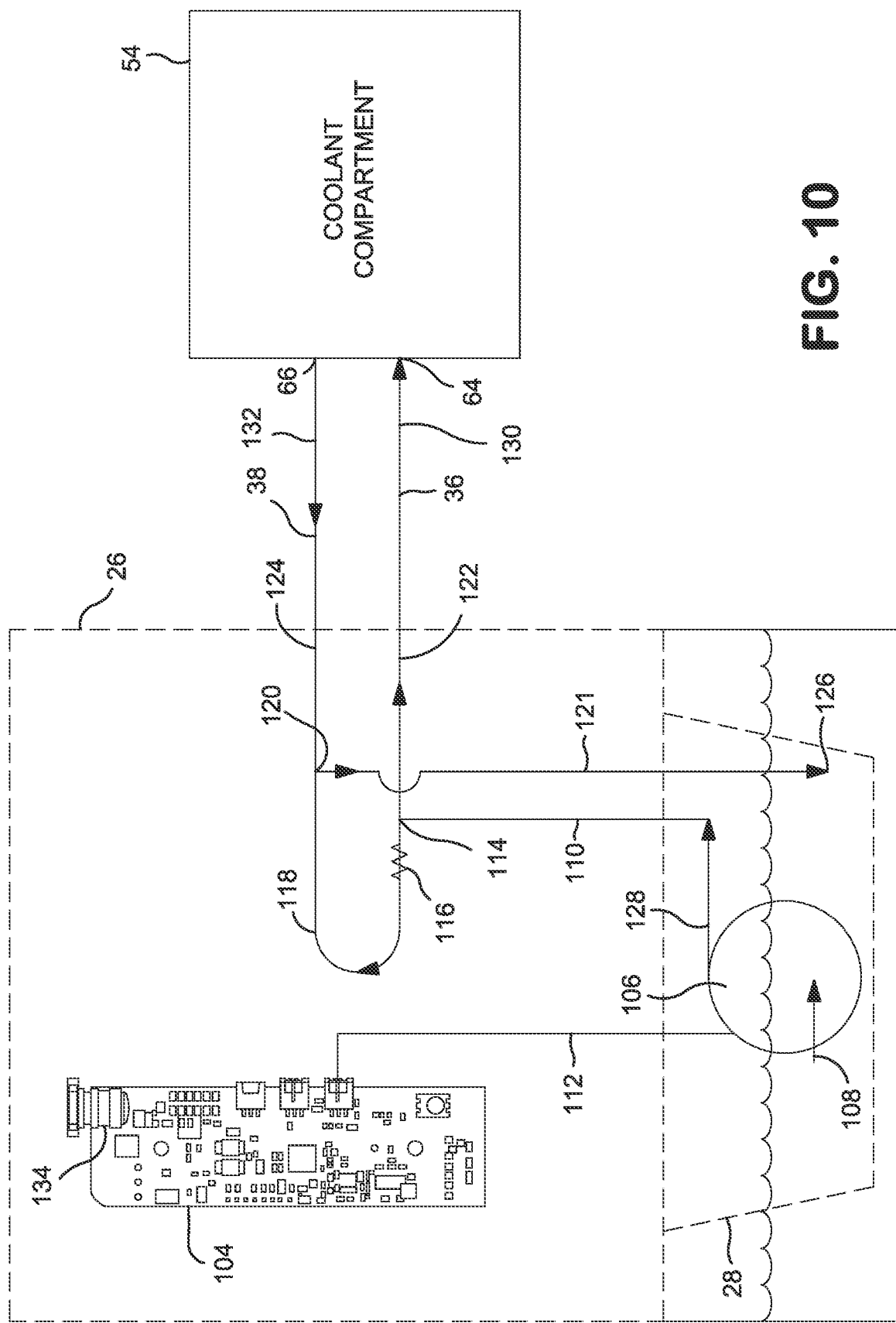
FIG. 10 is a structural schematic of a cold therapy module having utility in the integrated cold therapy-compression therapy assembly of FIG. 1, wherein a coolant flowpath through the cold therapy module is shown while performing a continuous cooling cycle.

Referring to FIGS. 7 and 10, a coolant pump 106, a coolant pump inlet 108, a coolant pump outlet line 110, a coolant pump power line 112, a first or inlet coolant manifold 114, a coolant pressure relief valve (PRV) 116, a PRV recirculation loop 118, a second or outlet coolant manifold 120, a coolant reservoir return line 121 and internal segments 122, 124 of the coolant inlet and outlet lines 36, 38 are among the internal operational components used to perform the cold therapy mode that are housed in the reservoir lid 22. More specifically with reference to FIG. 17, the coolant pump 106 and the coolant pump inlet 108 are housed in the lower portion 28 of the reservoir lid 22. In addition a discharge end 126 of the coolant reservoir return line 121 and an inlet end 128 of the coolant pump outlet line 110 exiting the coolant pump 106 are housed in the lower portion 28 of the reservoir lid 22. The remaining internal operational components used to perform the cold therapy mode are housed in the upper portion 26 of the reservoir lid 22. A fluid-tight seal is preferably provided between the upper and lower portions 26, 28 of the reservoir lid 22 such that there is no direct fluid communication between the interiors of the upper and lower portions 26, 28 except via the fully-contained coolant flow lines. Thus, moisture-sensitive components housed in the upper portion 26 of the reservoir lid 22 such as the PCBA 104 are protected against damage caused by the intrusion of coolant that is circulating through the cold therapy module.

The above-listed components 106, 108, 110, 112, 114, 116, 118, 120, 121, 122, 124 along with external segments 130, 132 of the coolant inlet and outlet lines 36, 38, the coolant compartment 54 of the bladder 46 and the shared PCBA 104 make up the cold therapy module of the integrated cold therapy-compression therapy assembly 10. The microprocessor of the PCBA 104 additionally controls operation of the coolant pump 106 and the PCBA 104 has a power jack 134 mounted thereon. The single-prong male plug on the end of the assembly power line 32 is connectable to the power jack 134, thereby supplying 12V DC, 1 A power from the AC to DC power converter at the opposite end of the assembly power line 32 to the PCBA 104 and correspondingly to the microprocessor and other electrical components of the compression and cold therapy modules.

The compression therapy module of the integrated cold therapy-compression therapy assembly 10 performs the compression therapy mode of operation in a manner described hereafter with reference to FIGS. 8, 9, 11, 12 and 13. The compression therapy mode of operation is characterized as an intermittent mode of operation that is effected by serially inflating and deflating the compressant compartment 52 of the bladder 46 while the treatment pad 16 is mounted on the body part being treated. The control panel 30 enables user controlled activation and deactivation of the compression therapy mode of operation. Once activated the microprocessor of the PCBA 104 and the firmware embedded therein direct automatic operation of the compression therapy module until the user elects to manually cease operation via the control panel 30.

Figure 14:
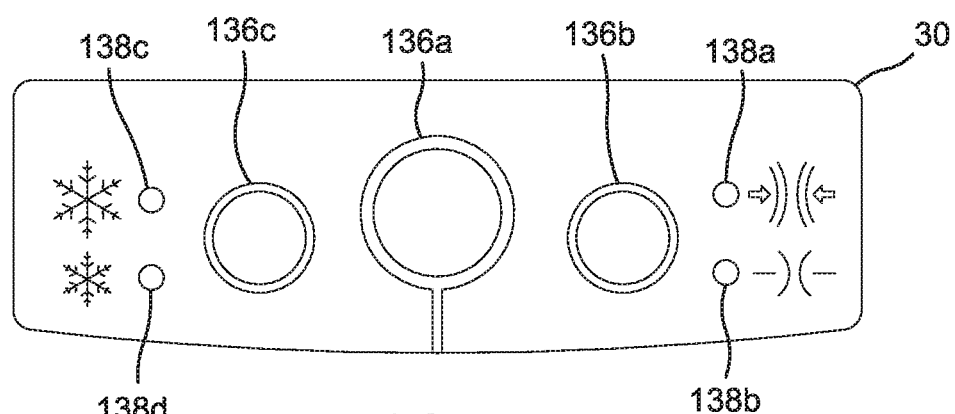
FIG. 14 is a view of a control panel having utility in the integrated cold therapy-compression therapy assembly of FIG. 1.

With additional reference to FIG. 14, the input of the control panel 30 is a plurality of hard or soft keys 136a, 136b, 136c forming a keypad. The output of the control panel 30 is a plurality of lights 138a, 138b, 138c, 138d which are preferably light emitting diodes (LED's) adjacent to or integral with the keys 136. The lights 138 function as visual operating status indicators for the user. The user initiates operation by pressing the on/off power key 136a to power up the integrated cold therapy-compression therapy assembly 10. When the integrated cold therapy-compression therapy assembly 10 is powered up (turned on or activated), the power key 136a illuminates. The user initiates the compression therapy mode of operation by pressing the compression therapy key 136b one or more times which toggles the compression therapy module to one of two desired active compression therapy settings, i.e., either regular or low, or to an inactive (off) compression therapy setting as indicated by lights 138a, 138b. Light 138a is an indicator that the regular compression therapy setting has been selected when it is Illuminated and light 138b is an indicator that the low compression therapy setting has been selected when it is Illuminated. When neither light 138a, 138b is illuminated, this indicates that the compression therapy module is in the inactive off setting. The user can switch between the two active compression therapy settings as well as the inactive off setting at any time during a given therapy session simply by re-toggling the compression therapy key 136b. Regardless of whether the compression therapy module is operating at the regular or low compression therapy setting, compression therapy comprises four sequential stages: inflation, hold, deflation and dwell. All four stages are operated under the direction of the microprocessor of the PCBA 104 in an automatic manner. The term "automatic" is used herein to mean that no user input is required for operation of the compression therapy module in accordance with the description below. The only user input permitted is manual selection of the active or inactive settings. The microprocessor selects the values for all the operating variables of the compression therapy mode of operation from its internal memory and/or firmware.

Figure 11:
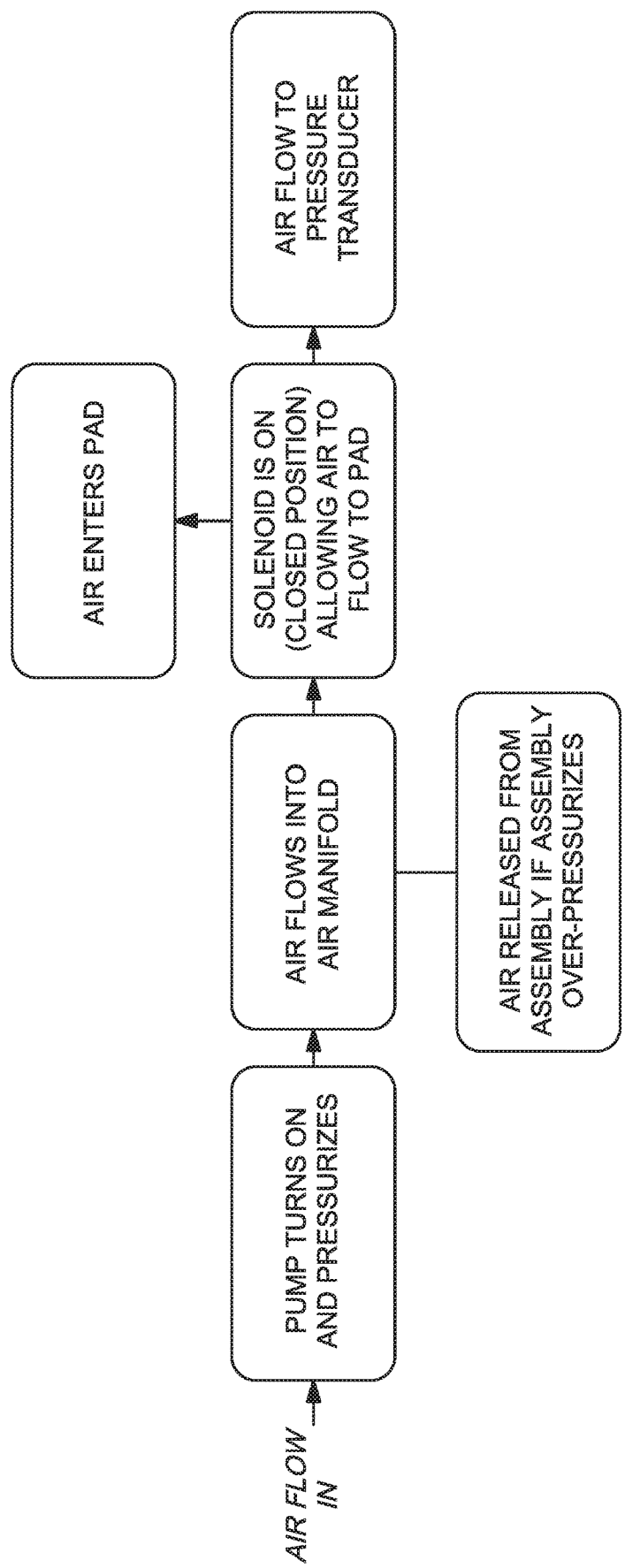
FIG. 11 is a flowchart showing performance of the pad inflation stage.

Referring to FIGS. 8 and 11, when the user presses the compression therapy key 136b in the correct sequence to select the regular compression therapy setting, the PCBA 104 responds by powering (activating) the compressant solenoid 88 via the solenoid power line 90 and turning on the compressant pump 80 via the compressant pump power line 86 which initiates the inflation stage of compression therapy. The compressant solenoid 88 is essentially an electronically activated vent that has an open position and a closed position. When unpowered (inactive), the compressant solenoid 88 is biased to its open position which is its default position. Powering the compressant solenoid 88 transitions it from its biased default open position to its closed position. Because the compressant solenoid 88 is located at the compressant manifold 92, transitioning the compressant solenoid 88 from the open position to the closed position seals the compression therapy module off from the surrounding atmosphere downstream of the compressant pump 80.

The activated compressant pump 80, which in the present case is essentially a gas compressor, draws the compressant, which is preferably air from the surrounding atmosphere at ambient pressure, into the compressant pump 80 via the compressant pump inlet 82. The compressant pump 80 operates at an inflation stage output level to compress the ambient air, thereby transforming it to pressurized air. The resulting pressurized air is directed from the compressant pump 80 through the compressant pump outlet line 84 and compressant manifold 92, past the closed compressant solenoid 88 and through the compressant inlet/outlet line 40 and compressant inlet/outlet port 68 into the compressant compartment 52 of the treatment pad 16. As such, the compressant pump outlet line 84, compressant manifold 92, compressant inlet/outlet line 40 and compressant inlet/outlet port 68 define a compressant inlet flowpath between the compressant pump 80 and compressant compartment 52, wherein the compressant solenoid 88 is positioned in the compressant inlet flowpath.

The compressant pump 80 increases the pressure in the compression treatment module from a pressure at or near ambient at the outset of the inflation stage until a regular peak pad pressure is reached in the compressant compartment 52. The regular peak pad pressure is a fixed predetermined pressure value that has preferably been previously entered into the microprocessor of the PCBA 104, typically at the time of manufacture and/or before distribution of the integrated cold therapy-compression therapy assembly 10 to users. An exemplary preferred regular peak pad pressure at the regular compression therapy setting is 50 mm Hg±5 gauge pressure. Nevertheless, this is only one example of a regular peak pad pressure having utility herein and others may be possible within the purview of the skilled artisan.

The air pressure in the compression therapy module is monitored at all times during operation of the integrated cold therapy-compression therapy assembly 10 using the pressure transducer 94 that communicates with the microprocessor in the PCBA 104. Once the pressure transducer 94 detects a compressant pressure in the pressure transducer line 96 that corresponds to the regular peak pad pressure in the compressant compartment 52, the PCBA 104 terminates the inflation stage and switches the compression therapy module to the hold stage. In accordance with the hold stage, the PCBA 104 slows the compressant pump 80 to a lower hold stage output level that is sufficient to maintain the regular peak pad pressure in the compressant compartment 52 constant. The PCBA 104 also maintains the compressant solenoid 88 powered and in the closed position for a hold time which is the total desired time duration of the hold stage. The hold time is a fixed predetermined time period that has preferably been previously entered into the microprocessor of the PCBA 104. When the hold time expires, the PCBA 104 terminates the hold stage and switches the compression therapy module to the deflation stage.

Figure 12:
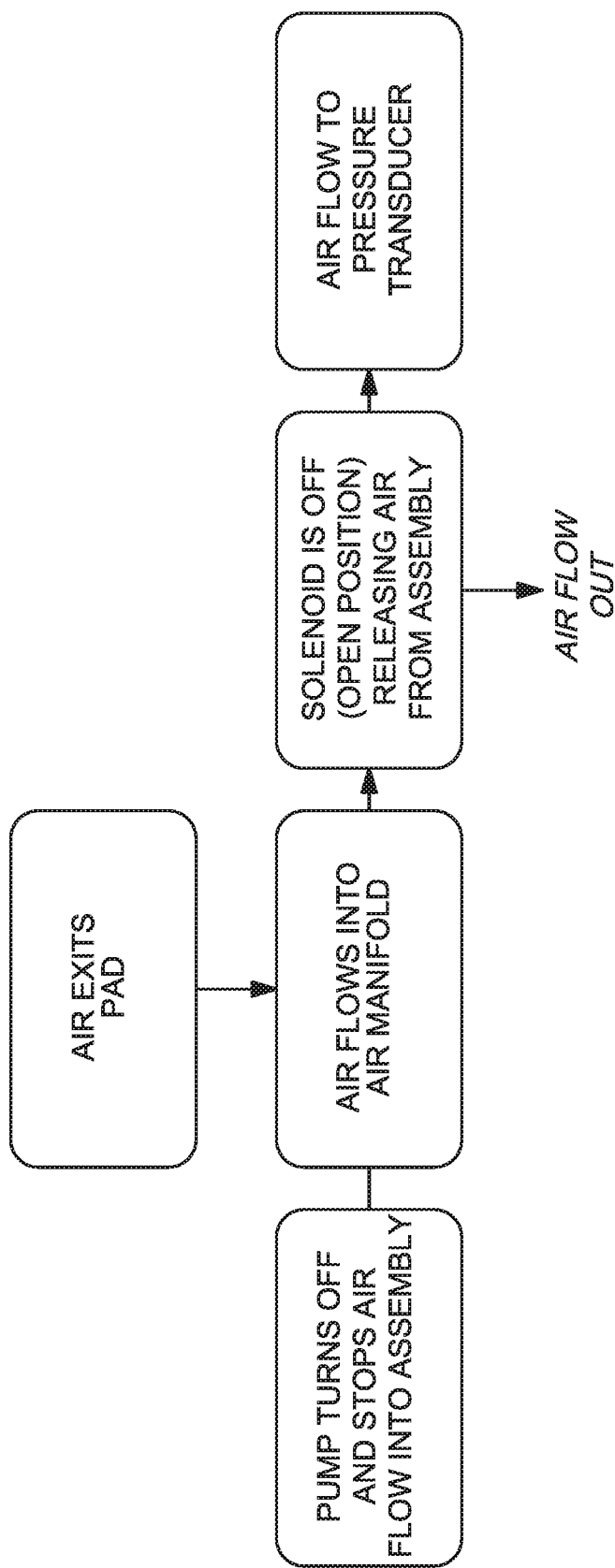
FIG. 12 is a flowchart showing performance of the pad deflation stage.

In the deflation stage described with reference to FIGS. 9 and 12, the PCBA 104 unpowers (turns off or inactivates) the compressant pump 80 and also unpowers the compressant solenoid 88, thereby automatically switching the compressant solenoid 88 to its biased default open position. Once the compressant pump 80 is turned off and inactive, the back pressure on the pressurized air in the compressant compartment 52 of the treatment pad 16 is released which causes the pressurized air in the compressant compartment 52 to flow back out of the compressant compartment 52 through the compressant inlet/outlet port 68, compressant inlet/outlet line 40 and compressant manifold 92 to the open compressant solenoid 88 which vents the pressurized air from the compressant compartment 52 in addition to any pressurized air from elsewhere in the compression therapy module to the surrounding atmosphere. As such, the compressant inlet/outlet port 68, compressant inlet/outlet line 40 and compressant manifold 92 define a compressant outlet flowpath between the compressant compartment 52 and compressant solenoid 88. Compressant outlet flowpath is a truncated version of the compressant inlet flowpath insofar as the compressant pump outlet line 84 is omitted from the compressant outlet flowpath, but in all other respects the compressant outlet and inlet flowpaths are the same.

Venting the pressurized air decreases the resulting pressure in the compressant compartment 52 from the regular peak pad pressure at the end of the inflation stage and duration of the hold stage to a minimum pad pressure. The minimum pad pressure is a fixed predetermined pressure value that has preferably been previously entered into the microprocessor of the PCBA 104. The minimum pad pressure is substantially less than the regular peak pad pressure and is preferably at or near ambient pressure. However, the minimum pad pressure does not typically drop to precisely ambient pressure because resistance to flow in the components of the compression therapy module may maintain a positive air pressure above ambient in the compression therapy module even when the compression therapy module is fully vented to the atmosphere. An exemplary preferred minimum pad pressure at the regular compression therapy setting is 0-10 mm Hg gauge pressure. Nevertheless, this is only one example of a minimum pad pressure having utility herein and others may be possible within the purview of the skilled artisan.

Once the pressure transducer 94 detects a compressant pressure in the pressure transducer line 96 that corresponds to the minimum pad pressure in the compressant compartment 52, the PCBA 104 terminates the deflation stage and switches the compression therapy module to the dwell stage. The compressant pump 80 remains unpowered or inactive (turned off) and the compressant solenoid 88 remains unpowered and biased to its default open position for the duration of the dwell stage, thereby maintaining the minimum peak pad pressure in the compressant compartment 52 for a dwell time which is the total desired time duration of the dwell stage. The dwell time is a fixed predetermined time period that has preferably been previously entered into the microprocessor of the PCBA 104. When the dwell time expires, the PCBA 104 terminates the dwell stage and a first cycle of the compression therapy mode of operation is completed.

Figure 13:
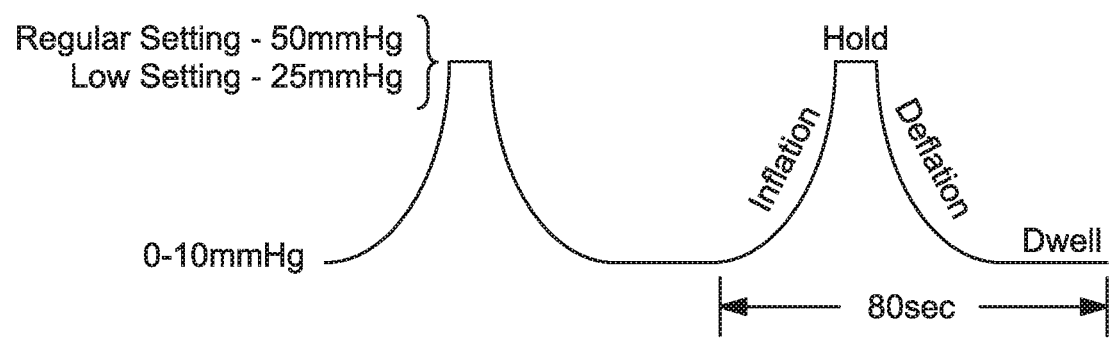
FIG. 13 is a graphical representation of a full compression therapy cycle.

As noted above, the user can switch from the regular compression therapy setting to the low compression therapy setting at any time during the therapy session simply by re-toggling the compression therapy key 136*b*. Alternatively, the user can select the low compression therapy setting at the outset of the therapy session. Regardless, operation of the compression therapy module at the low compression therapy setting is essentially the same as operation at the regular compression therapy setting except that the peak pad pressure is lower at the low compression therapy setting. An exemplary low peak pad pressure at the low compression therapy setting is 25 mm Hg±5. Nevertheless, this is only one example of a low peak pad pressure having utility herein and others may be possible within the purview of the skilled artisan. In any case, the low peak pad pressure is always lower than the regular peak pad pressure. FIG. 13 is a graphical representation of pressure (vertical axis) vs. time (horizontal axis) during the compression therapy mode of operation for one exemplary compression cycle at either a regular or low compression therapy setting.

Regardless of which active compression therapy setting is selected, it is often desirable during a single therapy session to operate in the compression therapy mode for multiple compression cycles, with each cycle immediately following the other, before terminating the compression therapy mode of operation. In such cases, when the PCBA 104 terminates the dwell stage, it immediately re-initiates the inflation stage of a second compression cycle and continues in this manner for as many compression cycles as are desired or until a desired total compression therapy time duration is reached. When a user desires to terminate the compression therapy mode of operation based on these criteria, the user simply re-toggles the compression therapy key 136*b* to the inactive (off) compression therapy setting. No intermittent compression therapy is performed at the off setting because the PCBA 104 turns off the compressant pump 80 and the compressant solenoid 88 is unpowered and biased in its default open position which vents the air in the compression therapy module to the surrounding atmosphere and prevents any further pressure build-up in the compression therapy module.

The compressant pressure relief valve (PRV) 98 is positioned at the compressant manifold 92. The compressant PRV 98 preferably remains biased closed at all times during operation of the integrated cold therapy-compression therapy assembly 10 except when the compression therapy module becomes over-pressurized and exceeds a predetermined safe compressant pressure limit. As such, the compressant PRV 98 is a redundant mechanical safety feature that prevents over pressurization of the compression therapy module. In the event the pressure at the compressant manifold 92 exceeds the compressant pressure limit, the compressant PRV 98 opens and vents the air in the compression therapy module to the surrounding atmosphere.

The cold therapy module of the integrated cold therapy-compression therapy assembly 10 performs the cold therapy mode of operation in a manner described hereafter with reference to FIGS. 10, 15, 16 and 17. The cold therapy mode of operation is characterized as a continuous mode of operation. The cold therapy mode is performed by continuously circulating the coolant between the coolant reservoir 12 and the coolant compartment 54 of the bladder 46 while the treatment pad 16 is mounted on the body part being treated. The control panel 30 enables user controlled activation and deactivation of the cold therapy mode of operation. Once activated the microprocessor of the PCBA 104 and the firmware embedded therein direct automatic operation of the cold therapy module until the user elects to manually cease operation via the control panel 30. The term "automatic" is likewise used herein to mean that no user input is required for operation of the cold therapy module in accordance with the description below.

Before initiating the cold therapy mode of operation, the user removes the reservoir lid 22 from the reservoir opening 24 of coolant reservoir 12 and fills the reservoir container 18 with a coolant and preferably a passive cooling medium through the reservoir opening 24. A preferred coolant is water and a preferred passive cooling medium is loose ice. After charging the coolant reservoir 12 with water and ice the user replaces the reservoir lid 22 over the reservoir opening 24 so that the bottom end of the lower portion 28 of the reservoir lid 22 and the bottom cover 29 extending therefrom are below the water line of the reservoir container 18 and submersed in the reservoir water therein. The coolant pump inlet 108 and discharge end 126 of the coolant reservoir return line 121 are positioned in the interior of the bottom cover 29 and are likewise submersed in the reservoir water within the reservoir container 18. The interior of the bottom cover 29 defines a chamber that is termed the "reservoir coolant mixing chamber" and more particularly the "reservoir water mixing chamber" because it is partially open to the intrusion of reservoir water therein from the surrounding reservoir container 18.

Although preferred, failure to submerse the discharge end 126 in the reservoir water, nevertheless, does not negate operation of the cold therapy module. The cold therapy module is fully operational as long as following conditions are satisfied: the coolant pump inlet 108 is submersed in the reservoir water; the discharge end 126 is positioned within the reservoir coolant mixing chamber proximal to the coolant pump inlet 108 and correspondingly within the interior of the reservoir container 18; and the discharge end 126 of the coolant reservoir return line 121 is in fluid communication with both the coolant pump inlet 108 and the interior of the reservoir container 18.

The submersed bottom cover 29 divides the reservoir water within the reservoir container 18 into two volumes. The first volume is reservoir water that is within the reservoir container 18 and is external to the bottom cover 29. The second volume is also reservoir water that is within the reservoir container 18, but unlike the first volume, the second volume is in the reservoir coolant mixing chamber internal to the bottom cover 29. The first volume of reservoir water is termed the "primary volume of coolant" or more particularly the "primary volume of reservoir water" and the second volume is termed the "secondary volume of coolant" or more particularly the "secondary volume of reservoir water" because the primary volume of reservoir water is preferably many times greater than the secondary volume of reservoir water.

Once the coolant reservoir 12 is charged and the treatment pad 16 is properly mounted on the user's body, the user initiates the cold therapy mode of operation by pressing the cold therapy key 136c (see FIG. 14) one or more times which toggles the cold therapy module to one of two desired active cold therapy settings, i.e., either colder or cold, or to an inactive (off) cold therapy setting as indicated by lights 138c, 138d. Light 138c is an indicator that the colder cold therapy setting has been selected when it is Illuminated and light 138d is an indicator that the cold cold therapy setting has been selected when it is Illuminated. When neither light 138c, 138d is illuminated, this indicates that the cold therapy module is in the inactive off setting. The user can switch between the two active cold therapy settings as well as the inactive off setting at any time during a given therapy session simply by re-toggling the cold therapy key 136c.

When the user presses the cold therapy key 136c in the correct sequence to select the colder cold therapy setting, the PCBA 104 responds by activating (turning on) the coolant pump 106 via the coolant pump power line 112 which initiates a startup transient of the cold therapy module that typically lasts up to several minutes. At the initiation of the startup transient all of the water in the reservoir container 18 has an essentially homogeneous cold temperature. As will be described hereafter, the primary volume of reservoir water maintains this same homogeneous cold temperature for the entire duration of the continuous cold therapy mode of operation even as the temperature of the secondary volume of reservoir water decreases with time relative to the temperature of the primary volume of reservoir water during the startup transient. This essentially constant homogeneous temperature reservoir water is termed "cold coolant" or more particularly "cold reservoir water" hereafter and its essentially constant temperature is termed the "cold coolant temperature" or more particularly the "cold reservoir water temperature." The primary volume of reservoir water is made up almost entirely of cold reservoir water which is at the cold reservoir water temperature.

Upon initiation of the startup transient, the activated coolant pump 106, which is preferably a centrifugal pump, draws cold reservoir water into it from the reservoir container 18 via the coolant pump inlet 108 that is submersed in the cold reservoir water. The coolant pump 106, which is under the control of the microprocessor in the PCBA 104, drives the cold reservoir water at a relatively higher pump speed dictated by the PCBA through the coolant pump outlet line 112, inlet coolant manifold 114, coolant inlet line 36 and coolant inlet port 64 into the coolant compartment 54 of the treatment pad 16. The actual value of the higher pump speed is a fixed predetermined speed that has preferably been previously entered into the microprocessor of the PCBA 104. In any case, the cold reservoir water follows the tortuous pad flowpath through the coolant compartment 54 between the coolant inlet and outlet ports 64, 66.

The temperature of the surface of the treatment pad 16 that contacts the body is termed the "treatment pad temperature." The cold reservoir water flowing through the coolant compartment 54 decreases the treatment pad temperature to a value that is well below the internal body temperature and is closer to the cold reservoir water temperature. Consequently conductive heat transfer between the body and the treatment pad 16 cools the part of the body on which the treatment pad 16 is mounted and simultaneously warms the cold reservoir water flowing through the pad flowpath in the coolant compartment 54 to the coolant outlet port 66. The reservoir water exiting the coolant compartment 54 via the coolant outlet port 66 is termed "warmed coolant" or more particularly "warmed reservoir water." The warmed reservoir water flows through the coolant outlet line 38, outlet coolant manifold 120 and coolant reservoir return line 121 back to the reservoir container 18 via the open discharge end 126 of the coolant reservoir return line 121. The discharge end 126 is positioned in the reservoir container 18 adjacent to the coolant pump inlet 108 so that they are in side by side relation with one another. The coolant outlet port 66, coolant outlet line 38, outlet coolant manifold 120, coolant reservoir return line 121 and discharge end 16 in combination define a warmed reservoir coolant flowpath or more particularly a warmed reservoir water flowpath that extends from the coolant compartment 54 to the reservoir container 18.

Upon exiting the discharge end 126 into the reservoir container 18, the warmed reservoir water mixes with the cold reservoir water residing in the reservoir container 18 to form a mixture, termed the "coolant inlet mixture" or more particularly the "reservoir water inlet mixture." As noted above, at the immediate outset of the startup transient, i.e., at initiation, only cold reservoir water is drawn into the coolant pump inlet 108. However, shortly after the warmed reservoir water first begins exiting the discharge end 126, the reservoir water inlet mixture replaces the solely cold reservoir water as the feed to the coolant pump 106 at the coolant pump inlet 108 and correspondingly replaces solely cold reservoir water as the feed to the coolant compartment 54 of the treatment pad 16. The coolant pump inlet 108, coolant pump 106, coolant pump outlet line 112, inlet coolant manifold 114, coolant inlet line 36 and coolant inlet port 64 in combination define a coolant inlet mixture flowpath or more particularly a reservoir water mixture flowpath that extends from the reservoir container 18 to the coolant compartment 54.

Continuous operation of the cold therapy module in the cold therapy mode as described above preferably achieves essentially steady-state operation following the startup transient. Over the course of the startup transient, the temperature of the reservoir water inlet mixture at the coolant inlet port 64, termed the "coolant inlet mixture temperature" or more particularly the "reservoir water inlet mixture temperature," and the temperature of the warmed reservoir water at the coolant outlet port 66, termed the "warmed coolant outlet temperature" or more particularly the "warmed reservoir water outlet temperature," decrease. Steady-state operation is reached when the coolant inlet mixture temperature and warmed coolant outlet temperature each attain and maintain a constant minimum value, wherein the constant minimum value for the warmed coolant outlet temperature is lower than the constant minimum value for the coolant inlet mixture temperature. Furthermore, at steady-state operation the ratio of the warmed reservoir water to the cold reservoir water in the reservoir water inlet mixture at the coolant pump inlet 108, termed the "coolant inlet ratio" or more particularly the "reservoir water inlet ratio," remains essentially constant over time.

An example of a preferred steady-state cold reservoir water temperature range is about 32-45° F. An example of a preferred steady-state reservoir water inlet mixture temperature range is about 38-50° F. An example of a preferred steady-state reservoir water outlet temperature range is about 42-52° F. An example of a preferred steady-state reservoir water inlet ratio range is between about 1:4 and about 1:10 warmed reservoir water to cold reservoir water.

The coolant pressure relief valve (PRV) 116 is positioned at the inlet coolant manifold 114. The coolant PRV 116 preferably remains biased closed at all times during operation of the integrated cold therapy-compression therapy assembly 10 except when the cold therapy module becomes over-pressurized and exceeds a predetermined safe coolant pressure limit. As such, the coolant PRV 116 is a mechanical safety feature that prevents over pressurization of the cold therapy module. In the event the pressure at the inlet coolant manifold 114 exceeds the coolant pressure limit, the coolant PRV 116 preferably only opens far enough to bleed off a relatively small amount of cold reservoir water from the coolant inlet line 36 that is sufficient to reduce the pressure in the coolant inlet line 36 below the coolant pressure limit. The bulk of the cold reservoir water in the coolant inlet line 36 preferably proceeds to the coolant compartment 54 in a normal manner via the coolant inlet port 64 while the bleed water flows through the coolant PRV 116 into the PRV recirculation loop 118. The PRV recirculation loop 118 directs the bleed water to the outlet coolant manifold 120 where it mixes with the warmed reservoir water from the coolant compartment 54. As such, the PRV recirculation loop 118 in combination with the coolant PRV 116 when it is open are a bleed coolant flowpath or more particularly a bleed water flowpath extending between the coolant inlet and coolant outlet manifolds 114, 120.

The mixture of bleed water and warmed reservoir water, termed the "outlet mixture," is returned to the reservoir container 18 via the discharge end 126. However, the ratio of the colder bleed water to the warmed reservoir water in the outlet mixture is generally so small that there is typically no appreciable difference between the temperature of the outlet mixture and the coolant outlet temperature. Furthermore, even if a relatively larger volume of the colder bleed water enters the outlet mixture and ultimately mixes into the reservoir water inlet mixture, the colder bleed water is so diluted by the warmed reservoir water and cold reservoir water in the reservoir water inlet mixture that the bleed water has minimal effect on the coolant inlet temperature.

Operation of the cold therapy module at the cold cold therapy setting is essentially the same as operation at the colder cold therapy setting except that the pump speed driving the cold reservoir water through the coolant pump outlet line 112, inlet coolant manifold 114 and coolant inlet line 36 is reduced to a relatively lower pump speed as dictated by the PCBA 104. The actual value of the lower pump speed is a fixed predetermined speed that has preferably been previously entered into the microprocessor of the PCBA 104. In any case, the reservoir water inlet mixture in the treatment pad 16 has a longer residence time in the treatment pad 16 and correspondingly a longer contact time with the body on which the treatment pad 16 is mounted due to the lower pump speed. As a result, and the reservoir water inlet mixture warms to a greater degree near the entrance to the coolant compartment 54 proximal to the coolant inlet port 64 and is not as cold further downstream in the coolant compartment 54 as the reservoir water inlet mixture flowing through the treatment pad 16 at the colder cold therapy setting. Thus, there is less of a cooling effect on the body part in contact with the treatment pad 16 when the cold therapy module is operating at the cold cold therapy setting.

The cold therapy module proceeds in a continuous steady-state mode of operation for as long as the user desires. When the user desires to terminate the cold therapy mode of operation, the user simply re-toggles the cold therapy key 136c to the inactive (off) cold therapy setting which causes the PCBA 104 to turn off the coolant pump 106, thereby ceasing fluid flow through the treatment pad 16.

Figure 17:
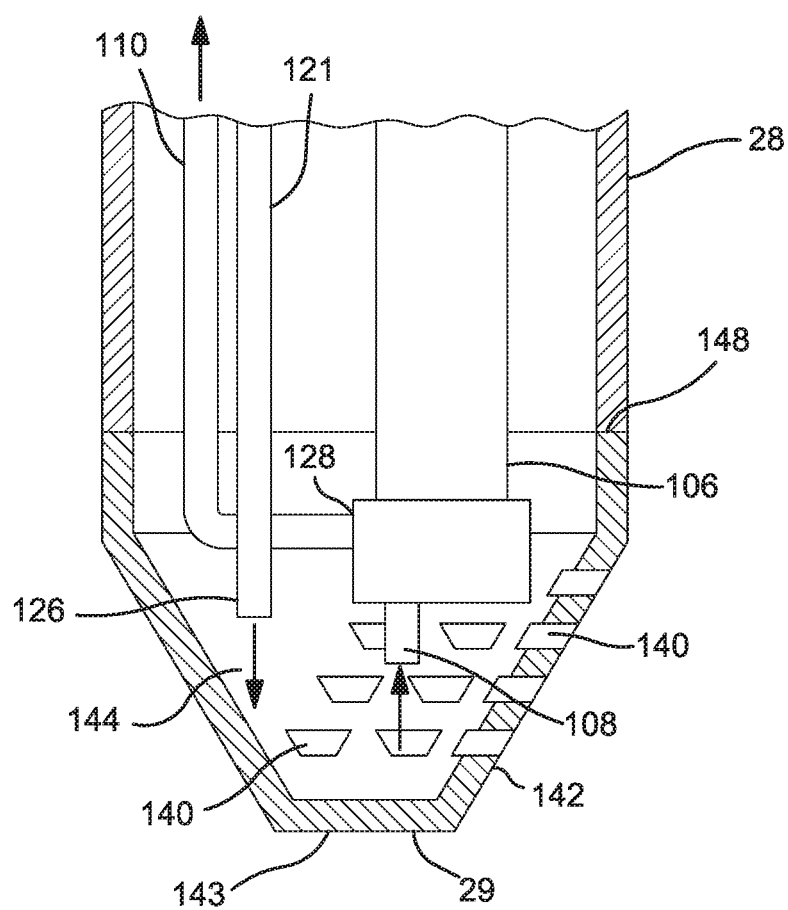
FIG. 17 is a partial side cross section of the bottom of the reservoir lid with the coolant port cover mounted thereon and having the same orientation as FIG. 15.

With specific reference to FIGS. 15-17, the bottom cover 29 of the reservoir lid 22 is a hollow shell that is constructed from a fluid-impervious plastic and that has an inverted conical configuration with a flared open upper end that tapers downward to a flattened closed lower end. Although the plastic is fluid-impervious, the bottom cover 29 is perforated by a plurality of coolant perforations or openings 140. The coolant openings 140 are slot-shaped holes in the bottom cover 29 through which liquids such as reservoir water are able to flow freely without substantial impediment. However, the coolant openings 140 are preferably sized to prevent passage of certain solids therethrough. In particular, the coolant openings 140 are sized to prevent ice chunks in the reservoir container 18 from passing through the bottom cover 29 into the reservoir coolant mixing chamber where the coolant pump inlet 108 and discharge end 126 reside.

In accordance with the present embodiment, coolant openings 140 are only provided across part of the bottom cover 29 rather than across the entire expanse of the bottom cover 29. As a result, the remainder of the bottom cover 29 lacking coolant openings is a continuously closed to block fluid flow. The particular bottom cover 29 shown in FIGS. 15-17 by way of example is a shell having a sloped side wall 142 defining a conical section that tapers downwardly. The downward end of the taper intersects with a substantially horizontal lower wall 143 that closes the lower end of the bottom cover 29. Only a part of the side wall 142 forming an arc about of about 300° has coolant openings 140 formed in it. This part is termed a "perforated wall panel." The remainder of the side wall 142 is designated 144 and is free of coolant openings and is continuously closed. The remainder and forms an arc about of about 60°. The remainder 144 is termed an "unperforated panel" or alternatively a "diverter panel." The diverter panel 144 is continuously fluid-impermeable such that reservoir water is unable to flow through it in either direction. The diverter panel 144 preferably occupies about 5-40% of the area of the side wall 142 and more preferably about 10-25% of the area of the side wall 142. In addition the lower wall 143, like the diverter panel 144, is also free of coolant openings.

The diverter panel 144 is preferably positioned proximal to the open discharge end 126 of the coolant reservoir return line 121 when the bottom cover 29 is properly mounted on the lower portion 28 of the reservoir lid 22. During operation of the cold therapy module warmed reservoir water returning from the treatment pad 16 to the reservoir container 18 disperses radially outward a full 360° as well as downwardly when it exits the discharge end 126. The stream of warmed reservoir water that disperses radially outward in an approximate 60° arc opposite the coolant pump inlet 108 is desirably prevented from channeling directly through the side wall 142 and exiting the reservoir coolant mixing chamber by the diverter panel 144. The diverter panel 144 diverts or deflects this stream of warmed reservoir water that is initially flowing away from the coolant pump inlet 108 by reversing its flow direction back toward the coolant pump inlet 108 within the reservoir coolant mixing chamber. As such the diverted stream of warmed reservoir water never exits the reservoir coolant mixing chamber and remains in the secondary volume of reservoir water, thereby avoiding mixing with the primary volume of reservoir water. In addition any downwardly dispersed warmed reservoir water is likewise diverted back toward the coolant pump inlet 108 by the lower wall 143.

As the diverted stream of warmed reservoir water approaches the coolant pump inlet 108 in the reservoir coolant mixing chamber, the diverted stream of warmed reservoir water encounters and mixes with a stream of cold reservoir water that has passed through the coolant openings 140 into the reservoir coolant mixing chamber from the exterior of the bottom cover 29. This stream of cold reservoir water in the secondary volume of reservoir water within the reservoir coolant mixing chamber is very small relative to the much larger primary volume of cold reservoir water in the reservoir container 18 external to the bottom cover 29. The diverted stream of warmed reservoir water approaching the coolant pump inlet 108 also encounters and mixes with additional warmed reservoir water that exited the discharge end 126 at the same time as the diverted stream, but had dispersed in the direction of the coolant pump inlet 108 immediately upon exiting the discharge end 126 without requiring diversion. The resulting mixture of warmed and cold reservoir water, i.e., the reservoir water inlet mixture, enters the coolant pump inlet 108 and the coolant pump 106 drives the reservoir water inlet mixture to the coolant compartment 54 of the treatment pad 16 via the coolant pump outlet line 110, inlet coolant manifold 114, coolant inlet port 64 and coolant inlet line 36.

An alignment notch 146 is preferably provided in the peripheral edge 148 of the bottom cover 29 that receives a cooperative alignment peg 150 protruding from the lower portion of the reservoir lid 22 when the diverter panel 144 is properly aligned with the discharge end 126 of the coolant reservoir return line 121. The alignment notch 146 and alignment peg 150 ensure that the bottom cover 29 and discharge end 126 are not inadvertently misaligned when the bottom cover 29 is fitted onto the lower portion 28 of the reservoir lid 22.

The overall effect of the diverter panel 144 is to desirably moderate the treatment pad temperature by automatic means as an alternative to adjusting the treatment pad temperature by setting the speed of the coolant pump 106. Moderating the treatment pad temperature is desirable because if the treatment pad 16 becomes too cold there is a risk to the user of skin damage. To enhance the temperature moderating impact of the warmed reservoir water exiting the discharge end 126, the diverter panel 144 diverts a substantial fraction of this warmed reservoir water back to the coolant pump inlet 108 that would have otherwise channeled directly into the primary volume of reservoir water. Since the warmed reservoir water encounters and mixes with a much smaller volume of cold reservoir water inside the bottom cover 29, the diverter panel 144 causes the warmed reservoir water to have a much greater moderating effect on the treatment pad temperature than otherwise. If the diverter panel 144 was not present on the bottom cover 29 and coolant openings 140 were provided across the entire expanse of the bottom cover 29, a significantly greater fraction of the warmed reservoir water exiting the discharge end 126 would flow directly into the primary volume of reservoir water in the reservoir container 18. Once warmed reservoir water exits the reservoir coolant mixing chamber into the primary volume of reservoir water, the warmed reservoir water has almost no temperature moderating effect because: 1) the primary volume of reservoir water in the reservoir container 18 is so much greater than the volume of warmed reservoir water exiting the discharge end 126; and 2) the primary volume of reservoir water consists by and large of cold reservoir water.

It is apparent from the above that any warmed reservoir water mixing with the primary volume of reservoir water in the reservoir container 18 has little impact on the overall temperature of the cold reservoir water. Accordingly, the temperature of the cold reservoir water residing in the reservoir container 18 as a rule does not change significantly during the cold therapy mode of operation. In any case, the user is free to further cool the cold reservoir water in the reservoir container 18 at any time during the cold therapy mode of operation by pausing operation, removing the reservoir lid 22, withdrawing excess cold reservoir water (if necessary) from the reservoir container 18, adding more ice thereto, replacing the reservoir lid 22 and resuming operation.

A number of alternate features may be added to or substituted for certain features of the above-described embodiments of the integrated cold therapy-compression therapy assembly 10. For example, non-permanent software may be substituted for firmware in the microprocessor of the PCBA 104. Furthermore, the microprocessor of the PCBA 104 may be used to monitor the compression and cold therapy modules for error conditions during operation in addition to directing the compression and cold therapy modes of operation. In accordance with this embodiment and depending on the type of error detected, the PCBA 104 will shut down one or both of the compression and cold therapy modules and will either unpower (turn off or inactivate) the integrated cold therapy-compression therapy assembly 10 or will flash the illuminated power key 136a. Some errors are automatically logged into memory for manufacturer failure analysis. Examples of errors that the microprocessor looks for include: inflation pressure above or below a predetermined pressure limit, deflation pressure above a predetermined pressure limit, aberrant pressure spikes at any point during operation in the compression therapy mode, control panel connection failure and input voltage to the PCBA above a predetermined voltage limit.

The compression therapy and cold therapy modes of operation of the integrated cold therapy-compression therapy assembly 10 are described above as being performed simultaneously or separately. Separate operation encompasses independent operation of the two modes relative to one another. It could also encompass synchronized operation of the two modes relative to one another. For example, the compression therapy and cold therapy modes could be operated in series in accordance with a predetermined pattern under the direction of the firmware in the microprocessor to achieve a synergistic effect. The compression therapy module and cold therapy module are described above as being structurally integrated into a single integrated cold therapy-compression therapy assembly 10. It is further within the scope of the present invention to structurally separate the two modules from one another so that each module can be independently used as a standalone device in the absence of the other. Thus, all of the structural components included in the compression therapy module described herein can be re-assembled apart from the cold therapy module as a unitary compression therapy device solely capable of operating in the compression therapy mode as likewise described herein. Similarly all of the structural components included in the cold therapy module described herein can be re-assembled apart from the compression therapy module as a unitary cold therapy device solely capable of operating in the cold therapy mode as likewise described herein.

The integrated cold therapy-compression therapy assembly 10 may be provided with multiple treatment pads, wherein each is preferably designed to conform to the size and contours of a different specific body part. Exemplary treatment pads having utility herein are available from Breg, Inc., Carlsbad, CA, U.S.A. In particular, treatment pads having utility herein are core region pads, namely, back pads, shoulder pads, hip pads and knee pads, and extremity region pads, namely, foot/ankle pads. One or more treatment pads may be used at any given time during operation of the integrated cold therapy-compression therapy assembly 10 and are selected from a multiple pad set in correspondence with the body part undergoing treatment. If the body part undergoing treatment is changed at any time, the user simply changes out the existing treatment pad(s) to another treatment pad(s) from the set that conforms to the new body part being treated.

The integrated cold therapy-compression therapy assembly 10 is described above as providing cold therapy, the assembly 10 may be more generally characterized as providing non-ambient thermal therapy and the fluid being circulated through the treatment pad may be more generally characterized as a heat transfer fluid. Thermal therapy encompasses not only cold therapy, but also heat therapy. The above-described cold therapy module is readily adaptable within the purview of the skilled artisan to function as a heat therapy module by substituting a heated fluid for the coolant of the cold therapy module. The heated fluid elevates the treatment pad temperature to a temperature that is above the internal body temperature so that conductive heat transfer between the body and the treatment pad heats the part of the body on which the treatment pad is mounted and simultaneously cools the heated fluid flowing through the treatment pad.

It is further within the scope of the present invention and within the purview of the skilled artisan to modify the design of the diverter panel 144 (with respect to its size and/or location relative to the discharge end 126) and/or the shape and pattern of the coolant openings 140 from that shown and described herein to achieve a greater or lesser temperature moderating effect from the warmed reservoir water as desired. For example, the coolant inlet mixture temperature can be increased, thereby increasing the differential between the cold reservoir coolant temperature and the coolant inlet mixture temperature, by adding more coolant openings to the perforated panel, increasing the size of the coolant openings in the perforated panel, increasing the size of the perforated panel, which correspondingly decreases the size of the diverter panel and/or positioning the diverter panel further from the discharge end 126 from that shown and described herein. Conversely, the coolant inlet mixture temperature can be decreased, thereby decreasing the differential between the cold reservoir coolant temperature and the coolant inlet mixture temperature, by reducing the number of coolant openings in the perforated panel, reducing the size of the coolant openings in the perforated panel, decreasing the size of the perforated panel, which correspondingly increases the size of the diverter panel and/or positioning the diverter panel closer to the discharge end 126 from that shown and described herein.

While the forgoing preferred embodiments of the invention have been described and shown, it is understood that alternatives and modifications, such as those suggested and others, may be made thereto and fall within the scope of the present invention.

We claim:

1. A cold therapy device comprising:
   a reservoir container configured to contain a coolant;
   a reservoir coolant mixing chamber positioned within said reservoir container;
   a cover positioned within said reservoir container and enclosing said reservoir coolant mixing chamber, said cover dividing said coolant in said reservoir container into a primary volume of coolant external to said cover within said reservoir container and a secondary volume of coolant internal to said cover within said reservoir coolant mixing chamber, wherein said primary volume of coolant is made up of a cold reservoir coolant at a cold reservoir coolant temperature and said secondary volume of coolant is made up of a coolant inlet mixture at a coolant inlet mixture temperature greater than said cold reservoir coolant temperature, wherein said coolant inlet mixture includes a warmed reservoir coolant and a portion of said cold reservoir coolant mixed together in said reservoir coolant mixing chamber, wherein said warmed reservoir coolant has a warmed coolant outlet temperature greater than said coolant inlet mixture temperature, wherein said coolant inlet mixture has a coolant inlet ratio and said coolant inlet ratio and said coolant inlet mixture temperature are defined by relative proportions of said warmed reservoir coolant and said cold reservoir coolant in said coolant inlet mixture, and wherein said cover has a plurality of coolant openings formed therein enabling said portion of said cold reservoir coolant to enter said reservoir coolant mixing chamber from said primary volume of coolant external to said cover;
   a coolant pump having a coolant pump inlet and a coolant pump outlet, wherein said coolant pump inlet is positioned within said reservoir coolant mixing chamber and submersible in said coolant inlet mixture;
   a treatment pad having a coolant inlet port, a coolant outlet port and a pad flowpath wending through said treatment pad between said coolant inlet and outlet ports, wherein said coolant inlet mixture is transformed to said warmed reservoir coolant in said treatment pad;
   a coolant discharge for said warmed reservoir coolant, wherein said coolant discharge is positioned within said reservoir coolant mixing chamber;
   a coolant outlet line connected to said coolant outlet port and said coolant discharge;
   a coolant inlet line connected to said coolant pump outlet and said coolant inlet port;
   a warmed reservoir coolant flowpath extending from said pad flowpath through said coolant outlet port, said coolant outlet line and said coolant discharge to said reservoir coolant mixing chamber, thereby enabling flow of said warmed reservoir coolant from said pad flowpath to said reservoir coolant mixing chamber;
   a coolant inlet mixture flowpath extending from said reservoir coolant mixing chamber through said coolant pump inlet, said coolant pump, said coolant pump outlet, said coolant inlet line and said coolant inlet port to said pad flowpath, thereby enabling flow of said coolant inlet mixture from said coolant reservoir coolant mixing chamber to said pad flowpath; and
a diverter panel in said cover wherein said diverter panel is continuously fluid-impermeable and free of any coolant openings and is positioned adjacent to said coolant discharge and oriented relative to said coolant discharge and said coolant pump inlet such that said warmed reservoir coolant is dispersed from said coolant discharge in a direction away from said coolant pump inlet and is redirected in an opposing direction back toward said coolant pump inlet by said diverter panel.

2. The cold therapy device of claim 1 further comprising a reservoir lid, wherein said reservoir container has a top side with a reservoir opening and wherein said reservoir lid is selectively positionable over said reservoir opening to selectively cover or uncover said reservoir opening.

3. The cold therapy device of claim 2, wherein said cover is directly attached to said reservoir lid and is in contact therewith.

4. The cold therapy device of claim 1 further comprising a microprocessor controlling operation of said coolant pump.

5. The cold therapy device of claim 1 further comprising a coolant reservoir return line having an open end, wherein said open end is said coolant discharge, an inlet coolant manifold connecting said coolant pump outlet to said coolant inlet line, an outlet coolant manifold connecting said coolant outlet line to said coolant reservoir return line at another end of said coolant reservoir return line opposite said open end, a coolant pressure relief valve connected to said inlet coolant manifold and a pressure relief valve recirculation loop extending between said coolant pressure relief valve and said outlet coolant manifold, wherein said pressure relief valve recirculation loop and said coolant pressure relief valve when open provide a bleed coolant flowpath between said inlet and outlet coolant manifolds.

6. The cold therapy device of claim 1, wherein the entirety of said cover is submersible in said primary volume of coolant.

7. The cold therapy device of claim 1, wherein said reservoir container has a plurality of sides and said cover does not include any of said plurality of sides.

8. The cold therapy device of claim 1, wherein said coolant discharge is submersible in said coolant inlet mixture.

9. The integrated assembly of claim 8 further comprising a pressure transducer in fluid communication with said compressant inlet and outlet flowpaths to determine a compressant pressure and further comprising a communication link between said pressure transducer and said shared microprocessor.

10. The integrated assembly of claim 8, wherein said coolant reservoir containing said cold reservoir coolant comprises:
a reservoir opening in said reservoir container surrounded by a rim defining an opening shape and dimensions; and
a reservoir lid configured to selectively cover or uncover said reservoir opening,
wherein said reservoir lid has an upper portion and a lower portion,
wherein said upper portion has an outer top face, an inner bottom face and an upper portion perimeter with a perimeter shape and dimensions in correspondence with said opening shape and dimensions, thereby enabling said upper portion perimeter to closely engage said rim when said reservoir lid selectively covers said reservoir opening,
wherein said lower portion has a top end, a bottom end and an elongate shape that is narrower relative to said upper portion perimeter,
wherein said top end of said lower portion is integral with said inner bottom face of said upper portion and said lower portion extends away from said upper portion,
wherein said cover is fitted onto said bottom end of said lower portion,
wherein said lower portion of said reservoir lid houses said coolant pump, said coolant pump inlet, a lower segment of said coolant pump outlet and said coolant discharge,
wherein said upper portion of said reservoir lid houses an upper segment of said coolant pump outlet, an internal segment of said coolant inlet line, an internal segment of said coolant outlet line, said compressant pump inlet, said compressant pump, said compressant pump outlet line, said compressant manifold, said solenoid vent, an internal segment of said compressant inlet/outlet line and said shared microprocessor, and
wherein said upper portion is sealed against liquid intrusion from said lower portion or from outside said reservoir lid except for fluid passing through said upper portion while fully contained within said coolant pump outlet and said coolant inlet and outlet lines.

11. The integrated assembly of claim 10 further comprising a control panel having a user input/output mounted on said outer top face of said upper portion.

12. A cold therapy treatment method comprising:
storing a cold reservoir coolant in a reservoir container;
positioning a reservoir coolant mixing chamber and a cover enclosing said reservoir coolant mixing chamber within said reservoir container;
dividing said coolant in said reservoir container into a primary volume of coolant external to said cover within said reservoir container and a secondary volume of coolant internal to said cover within said reservoir coolant mixing chamber, wherein said primary volume of coolant is made up of said cold reservoir coolant at a cold reservoir coolant temperature and said secondary volume of coolant is made up of a coolant inlet mixture at a coolant inlet mixture temperature;
submersing said cover in said primary volume of coolant;
mixing said cold reservoir coolant from said primary volume of coolant with a warmed reservoir coolant in said reservoir coolant mixing chamber to form said coolant inlet mixture, wherein said warmed reservoir coolant has a warmed coolant outlet temperature higher than said cold reservoir coolant temperature and said coolant inlet mixture temperature is between said warmed coolant outlet temperature and said cold reservoir coolant temperature;
positioning a coolant pump inlet and a coolant discharge within said reservoir coolant mixing chamber;
drawing said coolant inlet mixture into a coolant pump from said reservoir coolant mixing chamber via said coolant pump inlet;
conveying said coolant inlet mixture from said coolant pump through a pump outlet, a coolant inlet line and a coolant inlet port into a coolant compartment in a treatment pad mounted on a body of a user, wherein said coolant inlet mixture is conveyed by means of said coolant pump operating at a first coolant pump speed and said treatment pad has a treatment pad temperature dependent at least in part on said coolant inlet mixture temperature;

conveying said coolant inlet mixture along a pad flowpath in said coolant compartment wending from said coolant inlet port to a coolant outlet port;

warming said coolant inlet mixture in said pad flowpath by means of heat transfer with the body to form said warmed reservoir coolant;

conveying said warmed reservoir coolant from said pad flowpath into said reservoir coolant mixing chamber via a coolant outlet line and said coolant discharge; and flowing said cold reservoir coolant into said reservoir coolant mixing chamber from said primary volume of coolant in said reservoir container external to said cover through a plurality of coolant openings formed in a perforated panel of said cover, wherein said cover has also a diverter panel free of any coolant openings, thereby preventing flow of fluid in either direction therethrough, wherein said diverter panel is positioned adjacent to said coolant discharge and oriented relative to said coolant discharge and said coolant pump inlet such that said warmed reservoir coolant is dispersed from said coolant discharge in a direction away from said coolant pump inlet and is redirected in an opposing direction back toward said coolant pump inlet by said diverter panel.

13. The cold therapy treatment method of claim 12, wherein coolant inlet mixture has a coolant inlet ratio of said warmed reservoir water to said cold reservoir water in a range between about 1:4 and about 1:10.

14. The cold therapy treatment method of claim 12, wherein said first coolant pump speed is reduced to a second coolant pump speed slower than said first coolant pump speed to increase said treatment pad temperature.

15. An integrated cold therapy-compression therapy assembly comprising:
 a compressant pump having a compressant pump inlet and a compressant pump outlet line;
 a treatment pad having a compressant compartment and a compressant inlet/outlet port opening into said compressant compartment and further having a coolant compartment with a coolant inlet port, a coolant outlet port and a pad flowpath wending through said coolant compartment between said coolant inlet and outlet ports;
 a compressant inlet/outlet line connected to said inlet/outlet compressant port;
 a compressant manifold connecting said compressant inlet/outlet line and said compressant pump outlet line;
 a compressant inlet flowpath including said compressant pump, said compressant pump outlet line, said compressant inlet/outlet line and said compressant inlet/outlet port, wherein said compressant inlet flowpath extends between said compressant pump inlet and said compressant compartment of said treatment pad;
 a solenoid vent having a biased open position and a closed position, wherein said solenoid vent is in said compressant inlet flowpath when in said closed position, thereby retaining a pressurized compressant in said compressant compartment;
 a compressant outlet flowpath including said compressant inlet/outlet port and said compressant inlet/outlet line, wherein said compressant outlet flowpath extends between said solenoid vent and said compressant compartment of said treatment pad, wherein said solenoid vent is in said compressant outlet flowpath when in said biased open position, thereby discharging said pressurized compressant in said compressant compartment from said compressant outlet flowpath;
 a reservoir container configured to contain a coolant;
 a reservoir coolant mixing chamber positioned within said reservoir container;
 a cover positioned within said reservoir container and enclosing said reservoir coolant mixing chamber, said cover dividing said coolant in said reservoir container into a primary volume of coolant external to said cover within said reservoir container and a secondary volume of coolant internal to said cover within said reservoir coolant mixing chamber, wherein said primary volume of coolant is made up of a cold reservoir coolant at a cold reservoir coolant temperature and said secondary volume of coolant is made up of a coolant inlet mixture at a coolant inlet mixture temperature greater than said cold reservoir coolant temperature, wherein said coolant inlet mixture includes a warmed reservoir coolant and a portion of said cold reservoir coolant mixed together in said reservoir coolant mixing chamber, wherein said warmed reservoir coolant has a warmed coolant outlet temperature greater than said coolant inlet mixture temperature, wherein said coolant inlet mixture has a coolant inlet ratio and said coolant inlet ratio and said coolant inlet mixture temperature are defined by relative proportions of said warmed reservoir coolant and said cold reservoir coolant in said coolant inlet mixture, and wherein said cover has a plurality of coolant openings formed therein enabling said portion of said cold reservoir coolant to enter said reservoir coolant mixing chamber from said primary volume of coolant external to said cover;
 a coolant pump having a coolant pump inlet and a coolant pump outlet, wherein said coolant pump inlet is positioned within said reservoir coolant mixing chamber and submersible in said coolant inlet mixture;
 a coolant discharge for said warmed reservoir coolant, wherein said coolant discharge is positioned within said reservoir coolant mixing chamber;
 a coolant outlet line connected to said coolant outlet port and said coolant discharge;
 a coolant inlet line connected to said coolant pump outlet and said coolant inlet port;
 a warmed reservoir coolant flowpath extending from said pad flowpath through said coolant outlet port, said coolant outlet line and said coolant discharge to said reservoir coolant mixing chamber, thereby enabling flow of said warmed reservoir coolant from said pad flowpath to said reservoir coolant mixing chamber;
 a coolant inlet mixture flowpath extending from said reservoir coolant mixing chamber through said coolant pump inlet, said coolant pump, said coolant pump outlet, said coolant inlet line and said coolant inlet port to said pad flowpath, thereby enabling flow of said coolant inlet mixture from said reservoir coolant mixing chamber to said pad flowpath; and
 a diverter panel in said cover wherein said diverter panel is continuously fluid-impermeable and free of any coolant openings and is positioned adjacent to said coolant discharge and oriented relative to said coolant discharge and said coolant pump inlet such that said warmed reservoir coolant is dispersed from said coolant discharge in a direction away from said coolant pump inlet and is redirected in an opposing direction back toward said coolant pump inlet by said diverter panel.

16. The integrated assembly of claim 15, wherein said solenoid vent is positioned at said compressant manifold.

17. The cold therapy device of claim 15 further comprising a coolant reservoir return line having an open end, wherein said open end is said coolant discharge, an inlet coolant manifold connecting said coolant pump outlet to said coolant inlet line, an outlet coolant manifold connecting said coolant outlet line to said coolant reservoir return line at another end of said coolant reservoir return line opposite said open end, a coolant pressure relief valve connected to said inlet coolant manifold and a pressure relief valve recirculation loop extending between said coolant pressure relief valve and said outlet coolant manifold, wherein said pressure relief valve recirculation loop and said coolant pressure relief valve when open provide a bleed coolant flowpath between said inlet and outlet coolant manifolds.

18. The integrated assembly of claim 15 further comprising a shared microprocessor controlling operation of said compressant pump, said solenoid valve and said coolant pump.

19. A cold therapy device comprising:
a reservoir container configured to contain a coolant;
a reservoir coolant mixing chamber positioned within said reservoir container;
a cover positioned within said reservoir container and enclosing said reservoir coolant mixing chamber, said cover dividing said coolant in said reservoir container into a primary volume of coolant external to said cover within said reservoir container and a secondary volume of coolant internal to said cover within said reservoir coolant mixing chamber, wherein said primary volume of coolant is made up of a cold reservoir coolant at a cold reservoir coolant temperature and said secondary volume of coolant is made up of a coolant inlet mixture at a coolant inlet mixture temperature greater than said cold reservoir coolant temperature, wherein said coolant inlet mixture includes a warmed reservoir coolant and a portion of said cold reservoir coolant mixed together in said reservoir coolant mixing chamber, wherein said warmed reservoir coolant has a warmed coolant outlet temperature greater than said coolant inlet mixture temperature, wherein said coolant inlet mixture has a coolant inlet ratio and said coolant inlet ratio and said coolant inlet mixture temperature are defined by relative proportions of said warmed reservoir coolant and said cold reservoir coolant in said coolant inlet mixture, wherein said cover has a plurality of coolant openings formed therein enabling said portion of said cold reservoir coolant to enter said reservoir coolant mixing chamber from said primary volume of coolant external to said cover, and wherein said cover is submersible in said primary volume of coolant;
a coolant pump having a coolant pump inlet and a coolant pump outlet, wherein said coolant pump inlet is positioned within said reservoir coolant mixing chamber and is submersible in said coolant inlet mixture;
a coolant discharge for said warmed reservoir coolant, wherein said coolant discharge is positioned within said reservoir coolant mixing chamber and is submersible in said coolant inlet mixture;
a coolant outlet line connected to said coolant outlet port and said coolant discharge;
a coolant inlet line connected to said coolant pump outlet and said coolant inlet port;
a warmed reservoir coolant flowpath extending from said pad flowpath through said coolant outlet port, said coolant outlet line and said coolant discharge to said reservoir coolant mixing chamber, thereby enabling flow of said warmed reservoir coolant from said pad flowpath to said reservoir coolant mixing chamber;
a coolant inlet mixture flowpath extending from said reservoir coolant mixing chamber through said coolant pump inlet, said coolant pump, said coolant pump outlet, said coolant inlet line and said coolant inlet port to said pad flowpath, thereby enabling flow of said coolant inlet mixture from said reservoir coolant mixing chamber to said pad flowpath; and
a diverter panel in said cover wherein said diverter panel is continuously fluid-impermeable and free of any coolant openings and is positioned adjacent to said coolant discharge and oriented relative to said coolant discharge and said coolant pump inlet such that said warmed reservoir coolant is dispersed from said coolant discharge in a direction away from said coolant pump inlet and is redirected in an opposing direction back toward said coolant pump inlet by said diverter panel.

20. A cold therapy device comprising:
a reservoir container configured to contain a coolant;
a reservoir coolant mixing chamber positioned within said reservoir container;
a cover positioned within said reservoir container and enclosing said reservoir coolant mixing chamber, said cover dividing said coolant in said reservoir container into a primary volume of coolant external to said cover within said reservoir container and a secondary volume of coolant internal to said cover within said reservoir coolant mixing chamber, wherein said primary volume of coolant is made up of a cold reservoir coolant at a cold reservoir coolant temperature and said secondary volume of coolant is made up of a coolant inlet mixture at a coolant inlet mixture temperature greater than said cold reservoir coolant temperature, wherein said coolant inlet mixture includes a warmed reservoir coolant and a portion of said cold reservoir coolant mixed together in said reservoir coolant mixing chamber, wherein said warmed reservoir coolant has a warmed coolant outlet temperature greater than said coolant inlet mixture temperature, wherein said coolant inlet mixture has a coolant inlet ratio and said coolant inlet ratio and said coolant inlet mixture temperature are defined by relative proportions of said warmed reservoir coolant and said cold reservoir coolant in said coolant inlet mixture, wherein said cover has a plurality of coolant openings formed therein enabling said portion of said cold reservoir coolant to enter said reservoir coolant mixing chamber from said primary volume of coolant external to said cover, and wherein said cover is submersible in said primary volume of coolant;
a coolant pump having a coolant pump inlet and a coolant pump outlet, wherein said coolant pump inlet is positioned within said reservoir coolant mixing chamber and is submersible in said coolant inlet mixture;
a coolant discharge for said warmed reservoir coolant, wherein said coolant discharge is positioned within said reservoir coolant mixing chamber and is submersible in said coolant inlet mixture;
a coolant outlet line connected to said coolant outlet port and said coolant discharge;
a coolant inlet line connected to said coolant pump outlet and said coolant inlet port;
a warmed reservoir coolant flowpath extending from said pad flowpath through said coolant outlet port, said coolant outlet line and said coolant discharge to said reservoir coolant mixing chamber, thereby enabling flow of said warmed reservoir coolant from said pad flowpath to said reservoir coolant mixing chamber;

a coolant inlet mixture flowpath extending from said reservoir coolant mixing chamber through said coolant pump inlet, said coolant pump, said coolant pump outlet, said coolant inlet line and said coolant inlet port to said pad flowpath, thereby enabling flow of said coolant inlet mixture from said reservoir coolant mixing chamber to said pad flowpath;

a diverter panel in said cover wherein said diverter panel is continuously fluid-impermeable and free of any coolant openings and is positioned adjacent to said coolant discharge and oriented relative to said coolant discharge and said coolant pump inlet such that said warmed reservoir coolant is dispersed from said coolant discharge in a direction away from said coolant pump inlet and is redirected in an opposing direction back toward said coolant pump inlet by said diverter panel;

a reservoir opening in said reservoir container surrounded by a rim defining an opening shape and dimensions; and a reservoir lid configured to selectively cover or uncover said reservoir opening, wherein said reservoir lid has an upper portion and a lower portion, wherein said upper portion has an outer top face, an inner bottom face and an upper portion perimeter with a perimeter shape and dimensions in correspondence with said opening shape and dimensions, thereby enabling said upper portion perimeter to closely engage said rim when said reservoir lid selectively covers said reservoir opening, wherein said lower portion has a top end, a bottom end and an elongate shape that is narrower relative to said upper portion perimeter, wherein said top end of said lower portion is integral with said inner bottom face of said upper portion and said lower portion extends away from said upper portion, wherein said cover is fitted onto said bottom end of said lower portion, wherein said lower portion of said reservoir lid houses said coolant pump, said coolant pump inlet, a lower segment of said coolant pump outlet and said coolant discharge, wherein said upper portion of said reservoir lid houses an upper segment of said coolant pump outlet, an internal segment of said coolant inlet line, an internal segment of said coolant outlet line and a shared microprocessor, and wherein said upper portion is sealed against liquid intrusion from said lower portion or from outside said reservoir lid except for fluid passing through said upper portion while fully contained within said coolant pump outlet and said coolant inlet and outlet lines.

* * * * *